United States Patent
Uckert et al.

(10) Patent No.: US 11,981,721 B2
(45) Date of Patent: *May 14, 2024

(54) TRANSPOSON-BASED TRANSFECTION SYSTEM FOR PRIMARY CELLS

(71) Applicant: Max-Delbrück-Centrum für Molekulare Medizin in der Helmholtz-Gemeinschaft, Berlin-Buch (DE)

(72) Inventors: Wolfgang Uckert, Berlin (DE); Mario Bunse, Berlin (DE); Julian Clauss, Berlin (DE); Zsuzsanna Izsvák, Berlin (DE)

(73) Assignee: Max-Delbrück-Centrum für Molekulare Medizin in der Helmholtz-Gemeinshcaft, Berlin-Buch (DE)

( * ) Notice: Subject to any disclaimer, the term of this patent is extended or adjusted under 35 U.S.C. 154(b) by 344 days.

This patent is subject to a terminal disclaimer.

(21) Appl. No.: 17/193,182

(22) Filed: Mar. 5, 2021

(65) Prior Publication Data

US 2022/0089671 A1 Mar. 24, 2022

Related U.S. Application Data

(62) Division of application No. 16/085,206, filed as application No. PCT/EP2017/056117 on Mar. 15, 2017, now Pat. No. 10,975,136.

(30) Foreign Application Priority Data

Mar. 15, 2016 (EP) .................... 16160345

(51) Int. Cl.
*C07H 21/02* (2006.01)
*A61P 31/00* (2006.01)
*A61P 35/00* (2006.01)
*C07H 21/04* (2006.01)
*C07K 14/725* (2006.01)
*C12N 5/10* (2006.01)
*C12N 9/12* (2006.01)
*C12N 15/113* (2010.01)
*C12N 15/85* (2006.01)
*C12N 15/90* (2006.01)

(52) U.S. Cl.
CPC .......... *C07K 14/7051* (2013.01); *A61P 31/00* (2018.01); *A61P 35/00* (2018.01); *C12N 5/10* (2013.01); *C12N 9/1241* (2013.01); *C12N 15/113* (2013.01); *C12N 15/85* (2013.01); *C12N 15/90* (2013.01); *C12Y 207/07* (2013.01); *C12N 2310/141* (2013.01); *C12N 2800/22* (2013.01); *C12N 2800/24* (2013.01); *C12N 2800/90* (2013.01); *C12N 2840/20* (2013.01)

(58) Field of Classification Search
CPC .................... C12N 15/113; A61K 2300/00
See application file for complete search history.

(56) References Cited

U.S. PATENT DOCUMENTS

| | | | |
|---|---|---|---|
| 9,181,527 | B2 | 11/2015 | Sentman |
| 2006/0228800 | A1 | 10/2006 | Lin et al. |
| 2007/0190617 | A1 | 8/2007 | Wu et al. |
| 2015/0051267 | A1 | 2/2015 | Fekete et al. |

FOREIGN PATENT DOCUMENTS

| | | |
|---|---|---|
| DE | 102011118018 | 4/2013 |
| WO | 2017/050884 | 3/2017 |

OTHER PUBLICATIONS

Amendola et al., "Regulated and mmultiple miRNA and siRNA delivery into primary cells by a lentiviral platform", Mol. Therapy Jun. 2009; 17(6):1039-1052.
Bialer, G. et al. "Selected murine residues endow human TCR with enhanced tumor recognition", J Immunol. Jun. 1, 2010;184(11):6232-41.
Bunse, M. et al. "RNAi-mediated TCR Knockdown Prevents Autoimmunity in Mice Caused by Mixed TCR Dimers Following TCR Gene Transfer", Molecular Therapy, vol. 22, No. 11, Jul. 22, 2014, pp. 1983-1991.
Choi et al., "Optimization of AAV expression cassettes to improve packaging capacity and transgene expression in neurons", 2014 Mol Brain 7:17-27.
Chung, K.H. et al. "Polycistronic RNA polymerase II expression vectors for RNA interference based on BIC/miR-155", Nucleic Acids Res. Apr. 13, 2006;34(7):e53.
Cohen C.J, et al. "Enhanced antitumor activity of T cells engineered to express T-cell receptors with a second disulfide bond", Cancer Res. Apr. 15, 2007;67(8):3898-903.
Cohen, C.J. et al. "Enhanced antitumor activity of murine-human hybrid T-cell receptor (TCR) in human lymphocytes is associated with improved pairing and TCR/CD3 stability", Cancer Res. Sep. 1, 2006;66(17):8878-86.

(Continued)

Primary Examiner — Amy H Bowman
(74) Attorney, Agent, or Firm — Meunier Carlin & Curfman LLC

(57) ABSTRACT

The present invention relates to the field of genetic engineering, in particular, to a transposon-based transfection kit suitable for transfection of primary cells, such as T cells, comprising mRNA encoding a transposase, or reagents for generating mRNA encoding said transposase, as well as minicircle DNA comprising the transposon. The invention also relates to a nucleic acid, preferably, a DNA minicircle, comprising a transposon, wherein the transposon encodes a protein and at least one miRNA, wherein the sequences encoding the miRNA are located in an intron and expression of the protein and the miRNA is regulated by the same promoter. The invention also provides a population of cells obtainable with the method of the invention. Methods of transfection are also provided, as well as medical use, e.g. in immunotherapy, in particular, in adoptive T cell therapy or T cell receptor (TCR) or chimeric antigen receptor (CAR) gene therapy.

16 Claims, 8 Drawing Sheets

Figure 3:
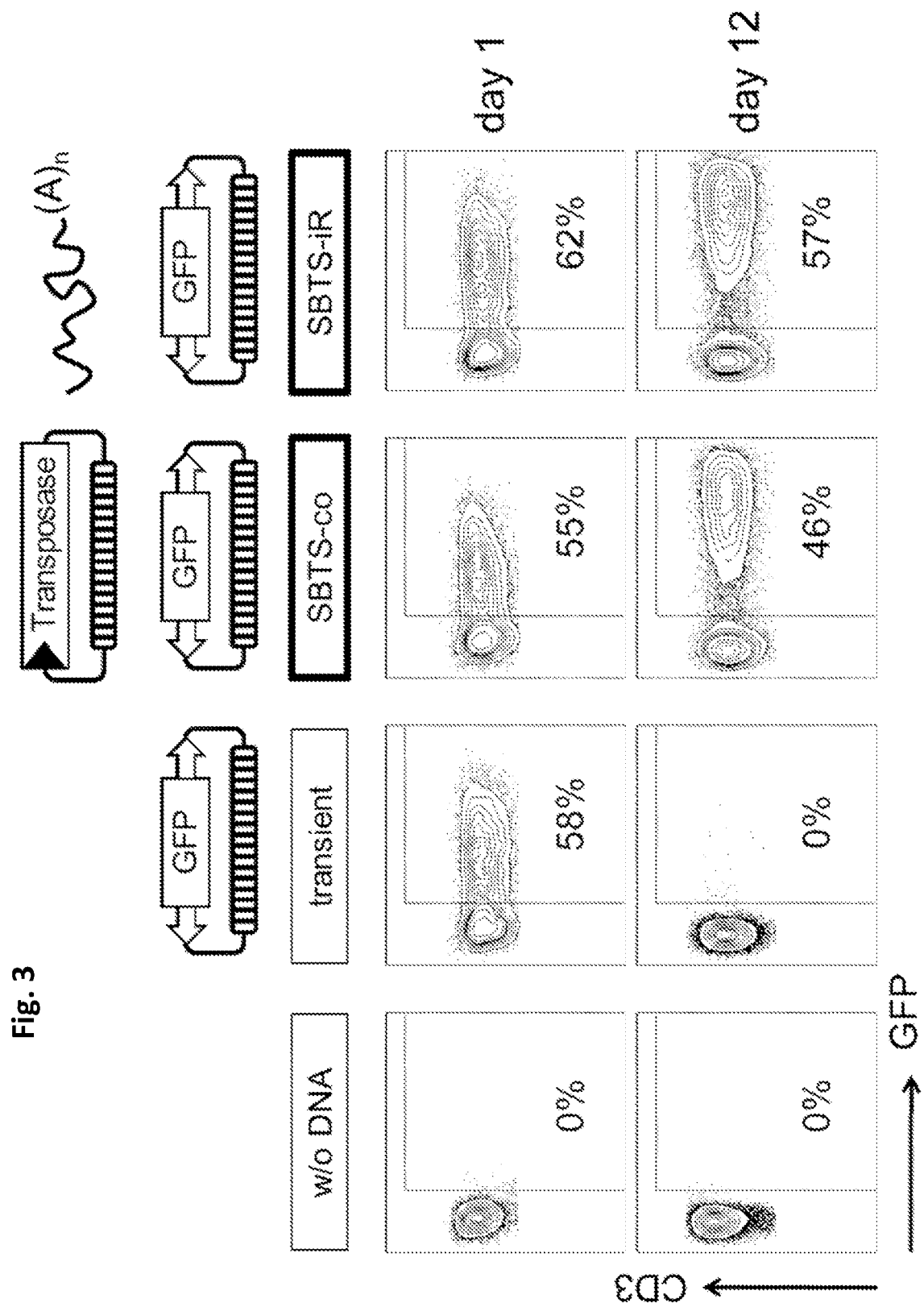

Specification includes a Sequence Listing.

(56) References Cited

OTHER PUBLICATIONS

Cui, Z. et al. "Structure-Function Analysis of the Inverted Terminal Repeats of the Sleeping Beauty Transposon", Journal of Molecular Biology, 318(5), 1221-1235 (2002).
Data sheet for pCI and pSI mammalian expression vectors, Promega Jul. 2009.
Deniger, D.C. et al. "Stable, Nonviral Expression of Mutated Tumor Neoantigen-specific T-cell Receptors Using the Sleeping Beauty Transposon/Transposase System", Molecular Therapy, vol. 24, No. 6, Mar. 5, 2016, pp. 1078-1089.
Engels, B. et al. "Retroviral vectors for high-level transgene expression in T lymphocytes", Human Gene Therapy, 14(12), 1155-1168 (2003).
Field, A. et al. "Comparison of Lentiviral and Sleeping Beauty Mediated [alpha][beta] T Cell Receptor Gene Transfer", PLOS One, vol. 8, No. 6, Jun. 28, 2013.
Galla, M. et al. "Avoiding cytotoxicity of transposases by does-controlled mRNA delivery", Nucleic Acids Research, vol. 39, No. 16, May 23, 2011, pp. 7147-7160.
Garrels, W. et al. "Cytoplasmic injection of murine zygotes with Sleeping Beauty transposon plasmids and minicircles results in the efficient generation of germline transgenic mice", Biotechnology Journal, vol. 11, No. 1, Oct. 16, 2015, pp. 17.
Gogol-Doring, A. et al. "Genome-wide Profiling Reveals Remarkable Parallels Between Insertion Site Selection Properties of the MLV Retrovirus and the piggyBac Transposon in Primary Human CD4+ T Cells", Molecular Therapy, vol. 24, No. 3, Mar. 1, 2016, pp. 592-606.
Halene S., et al. "Improved Expression in Hematopoietic and Lymphoid Cells in Mice After Transplantation of Bone Marrow Transduced With a Modified Retroviral Vector", Blood, Nov. 15, 1999 (Nov. 15, 1999), pp. 3349-3357.
Holstein, M. et al. "Efficient non-viral gene delivery by minicircle Sleeping Beauty transposon system into hematopoietic stem cells for genetherapy applications", Human Gene Therapy (ESGCT and FSGT collaborative congress),2015, vol. 26(10), p. A18:OR050.
International Search Report and Written Opinion dated May 30, 2017, from International Application No. PCT/EP2017/056117, 10 pages.
Ivics, Z. et al. "Molecular reconstruction of Sleeping Beauty, a Tc1-like transposon from fish, and its transposition in human cells", Cell. Nov. 14, 1997;91(4):501-10.
Jebbawi, F., et al. "A microRNA profile of human CD8+ regulatory T cells and characterization of the effects of microRNAs on Treg cell-associated genes." Journal of translational medicine 12.1 (2014): 218.
Jin, Z. et al. "The hyperactive Sleeping Beauty transposase SB100X improves the genetic modification of T cells to express a chimeric anitgen receptor", Gene Therapy, vol. 18, No. 9, Mar. 31, 2011, pp. 849-856.
Kay, M.A. et al. "A robust system for production of minicircle DNA vectors", Nat Biotechnol. Dec. 2010;28(12):1287-9.
Kuball, J. et al. "Facilitating matched pairing and expression of TCR chains introduced into human T cells", Blood. Mar. 15, 2007;109(6):2331-8.
Leisegang, M. et al. "Enhanced functionality of T cell receptor-redirected T cells is defined by the transgene cassette", Journal of Molecular Medicine, 86(5), 573-583 (2008).
Liddy, N. et al. "Monoclonal TCR-redirected tumor cell killing", Nat Med. Jun. 2012;18(6):980-7.
Mátés, L. et al. "Molecular evolution of a novel hyperactive Sleeping Beauty transposase enables robust stable gene transfer in vertebrates", Nat Genet. Jun. 2009;41(6):753-61.
Obenaus, M. et al. "Identification of human T-cell receptors with optimal affinity to cancer antigens using antigen-negative humanized mice", 33(4), Nature biotechnology, 402-407 (2015).
Office Action issued in European Application No. 17712722.2, dated Apr. 2, 2020, 9 pages.
Qasim W., et al. "Lentiviral Vectors for T-cell Suicide Gene Therapy: Preservation of Tcell Effector Function After Cytokine-mediated Transduction", Molecular Therapy, vol. 15, No. 2, Feb. 1, 2007 (Feb. 1, 2007), pp. 355-360, XP55680196, DOI: 10.1038/sj.mt.6300042.
Robbins, P.F. et al. "A pilot trial using lymphocytes genetically engineered with an NY-ESO-1-reactive T-cell receptor: long-term follow-up and correlates with response", Clin Cancer Res. Mar. 1, 2015;21(5):1019-27.
Rosenberg, S. A. et al. "Adoptive cell transfer: a clinical path to effective cancer immunotherapy", Nature Reviews Cancer, 8(4), 299-308 (2008).
Sætrom, P. et al. "Conserved MicroRNA Characteristics in Mammals", Oligonucleotides, 16(2), 115-144 (2006).
Sharma N., et al. "Efficient Sleeping Beauty DNA Transposition From DNA Minicircles", Molecular Therapy—Nucleic Acids, vol. 2, No. 2, Feb. 1, 2013 (Feb. 1, 2013), p. e74, XP055317219, DOI: 10.1038/mtna.2013.1.
Singh, H. et al. "Manufacture of clinical-grade CD19-specific T cells stably expressing chimeric antigen receptor using Sleeping Beauty system and artificial antigen presenting cells", PLoS One. 8:e64138 (2013).
Sommermeyer, D. et al. "Minimal amino acid exchange in human TCR constant regions fosters improved function of TCR gene-modified T cells", J Immunol. Jun. 1, 2010;184(11):6223-31.
Sumiyoshi T., et al. "Stable Transgene Expression in Primitive Human CD34 Hematopoietic Stem Progenitor Cells, Using the Sleeping Beauty Transposon System", Human Gene Therapy, vol. 20, No. 12, Dec. 1, 2009 (Dec. 1, 2009), pp. 1607-1626.
Vonderheide, R.H. et al. "Engineering T cells for cancer: our synthetic future", Immunol Rev. Jan. 2014 257(1):7-13.
Zhang, K.D. et al. "Expression and Misexpression of the miR-183 Family in the Developing Hearing Organ of the Chicken", PLOS One, vol. 10, No. 7, Jul. 15, 2015.
Peng, P. D., et al. "Efficient nonviral Sleeping Beauty transposon-based TCR gene transfer to peripheral blood lymphocytes confers antigen-specific antitumor reactivity." Gene therapy 16.8 (2009): 1042-1049.

Fig. 1
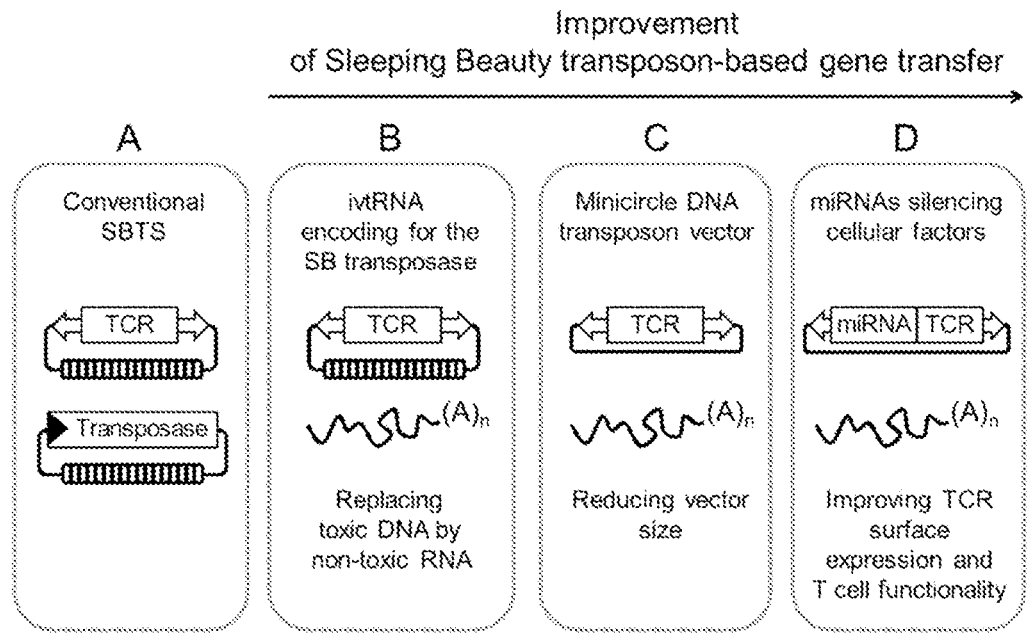
Fig. 2A
Fig. 2B
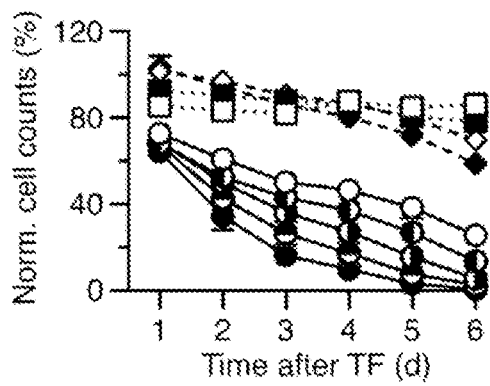
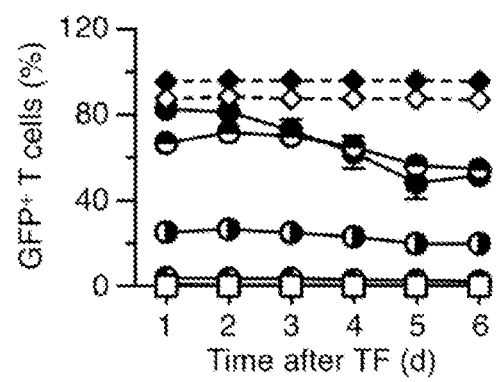
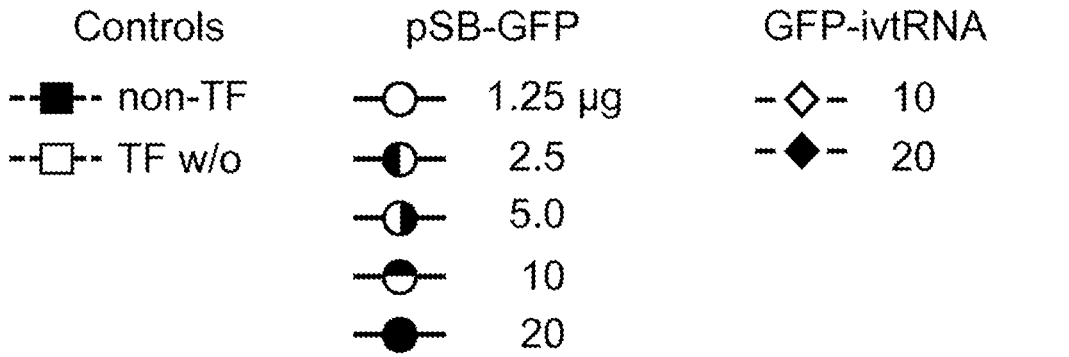

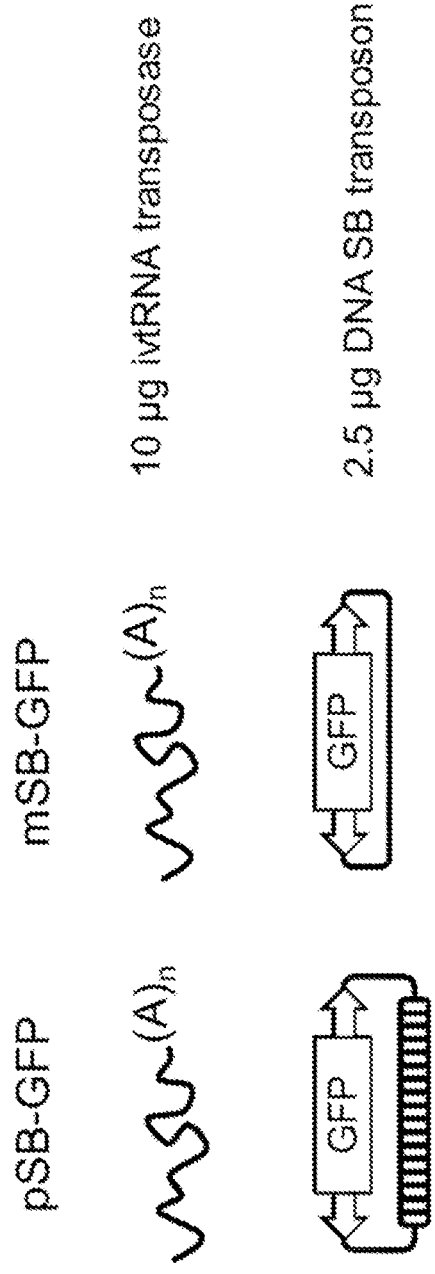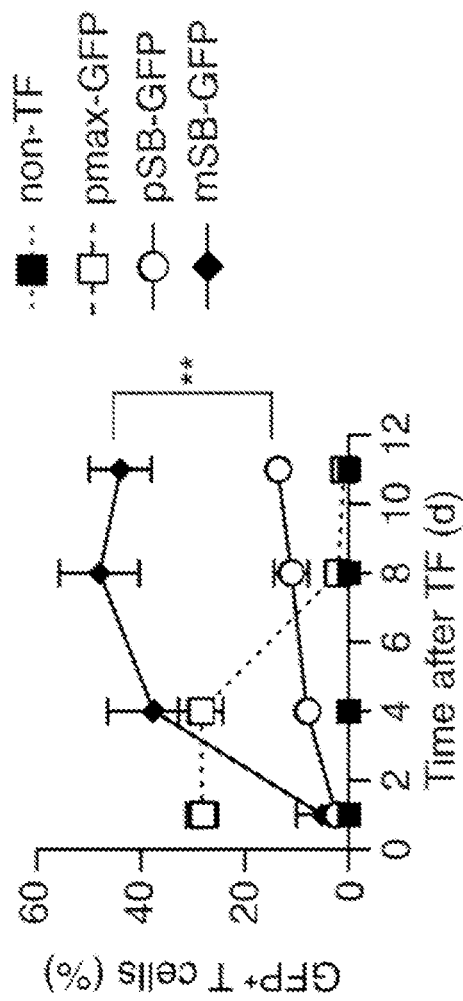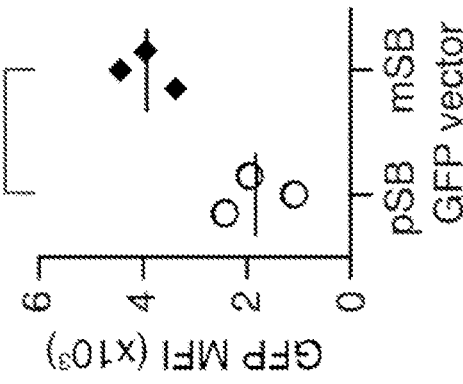

SB-GFP w/o

CD3 (MFI):
10910

SB-GFP w/ anti-TRAC 1x miRNA

CD3 (MFI):
2843

2x miRNA

CD3 (MFI):
1782

TRANSPOSON-BASED TRANSFECTION SYSTEM FOR PRIMARY CELLS

CROSS-REFERENCE TO RELATED APPLICATIONS

This application is a divisional application of U.S. application Ser. No. 16/085,206, filed on Sep. 14, 2018, which is a National Stage Application of PCT/EP2017/056117, filed Mar. 15, 2017, claims priority to foreign application EP 16160345.1, filed Mar. 15, 2016, the disclosures of which are incorporated herein by reference in their entirety.

The present invention relates to the field of genetic engineering, in particular, to a transposon-based transfection kit suitable for transfection of cell lines and primary cells, such as T cells, comprising mRNA encoding a transposase, or reagents for generating mRNA encoding said transposase, as well as minicircle DNA comprising the transposon. The invention also relates to a nucleic acid, preferably, a DNA minicircle, comprising a transposon, wherein the transposon encodes at least one protein and at least one miRNA, wherein the sequences encoding the miRNA are located in an intron and expression of the protein and the miRNA is regulated by the same promoter. The invention also provides a population of cells obtainable with the method of the invention. Methods of transfection are also provided, as well as medical use, e.g. in immunotherapy, in particular, in adoptive T cell therapy using T cell receptor (TCR) gene-modified T cells (TCR gene therapy) or chimeric antigen receptor (CAR) gene-modified T cells (CAR gene therapy).

Adoptive T cell therapy (ATT) is a promising immunotherapeutic strategy to treat cancer, chronic infections, and autoimmune diseases. ATT requires the preparation of large numbers of antigen-specific T cells that recognize and eradicate diseased cells. ATT involves on one hand the isolation, expansion, and reinfusion of naturally occurring, antigen-specific T cells into the patient to treat the disease. However with regard to cancer, most patients lack suitable amounts of naturally occurring antigen-specific T cells (tumor infiltrating lymphocytes, TILs) and moreover, these cells are difficult to isolate from many tumor entities. Therefore, ATT uses on the other hand host cells, which have been engineered with antigen receptor genes (TCR, CAR) to endow the cells with a new antigen specificity. ATT using CAR- and TCR-engineered T cells has been successfully employed to treat cancer and virus-associated diseases, refractory to other treatments (Vonderheide et al., 2014; Robbins et al., 2015).

TCR and CAR gene therapy necessitates the genetic engineering of large numbers of primary human T cells. This can be efficiently done using viral vector systems. However, the technology is laborious, time consuming, and costly. In contrast, the use of plasmid DNA-based transposon vector systems offers several advantages. The production of GMP grade vector (especially large-scale vector production) is faster, less labor-intensive, cost-saving and involves less bureaucratic burden. In addition, the transgene capacity of transposon vectors is larger in comparison to viral vectors and some transposons show a random integration pattern without preference for active genes.

A major drawback using conventional transposon vector systems consisting of two DNA plasmids (FIG. 1A) for the genetic modification of primary cells is the high cell mortality induced by transfection of DNA (FIG. 2A), which hampers rapid expansion of the transfected cells and needs fundamental optimization. Despite of this drawback, transposon-based methods have been successfully applied for the genetic engineering of primary cells, e.g., T cells. However, the conventional method is inefficient because most of the T cells die after transfection and only a small percentage of the surviving cells stably express the transgene. Two strategies were applied to obtain the required number of genetically modified T cells for therapy after the cells were transfected using the conventional method. First, the cells were selectively expanded with the help of a stimulator cell line presenting the specific ligand of the transferred antigen receptor (Singh et al., 2013). As a result, the generation of a new stimulator cell line for every antigen receptor with a new specificity is required. Furthermore, such selective outgrowth of the modified cells cannot be induced in situations where the specificity of the transferred antigen receptor is unknown or the transposon does not encode an antigen receptor. The second strategy is that the transfected cells were sorted for surface expression of the transferred TCR with the help of a specific antibody. Afterwards, the sorted cells were expanded using allostimulation (Deninger et al., 2016). This strategy requires the transfection of a TCR with full-length mouse constant regions, which are immunogenic in humans, and an antibody that is approved for clinical protocols. Furthermore, the sorted T cells are stimulated through their endogenous TCR in this protocol. Cells in which the transferred TCR completely replaced the endogenous TCR cannot be expanded this way. Therefore, allogeneic stimulation is inherently incompatible with the intent to generate cells for therapy that express as much as possible transferred TCR on their surface. Finally, neither selective expansion nor sorting of transfected cells directly addresses the issues of low transfection rates and high cell mortality. In conclusion, there is a considerable need to provide more efficient methods and kits for the genetic engineering of such cells, in particular of primary cells and other cells which are hard to transfect with reasonable efficacy.

This problem is solved by the present invention, in particular, by the subject matter of the claims.

The present invention provides a kit comprising
a) a nucleic acid encoding a transposase capable of mobilizing a transposon, wherein the nucleic acid is selected from the group comprising
 (i) mRNA encoding said transposase; or
 (ii) DNA encoding said transposase functionally linked to a promoter, wherein the kit optionally further comprises reagents suitable for in vitro transcription comprising ribonucleotide triphosphates, a buffer suitable for transcription, and a RNA polymerase suitable for transcription; and
b) minicircle DNA comprising said transposon, wherein the transposon encodes a protein and/or a miRNA, wherein expression of the protein and/or the miRNA is regulated by a promoter.

In the context of the present invention "a" does not exclusively refer to "one", but also encompasses "two or more". Accordingly, the transposon may encode one or more proteins and/or one or more miRNA. For example, the transposon may encode two proteins and one miRNA. Preferably, it encodes one protein and two (or more) miRNAs. Of course, it may also encode two proteins and two miRNAs.

In one embodiment, the nucleic acid of a) is mRNA which has been transcribed in vitro, i.e., ivtRNA (FIG. 1B). Purified RNA may also be used. RNA should be of high quality and high concentration, e.g., comparable to ivtRNA routinely obtained. Quality is determined (a) by the amount of mRNAs formed with a 5' cap analog, (b) the poly(A) tail and (c) purity of the RNA.

Figure 4:
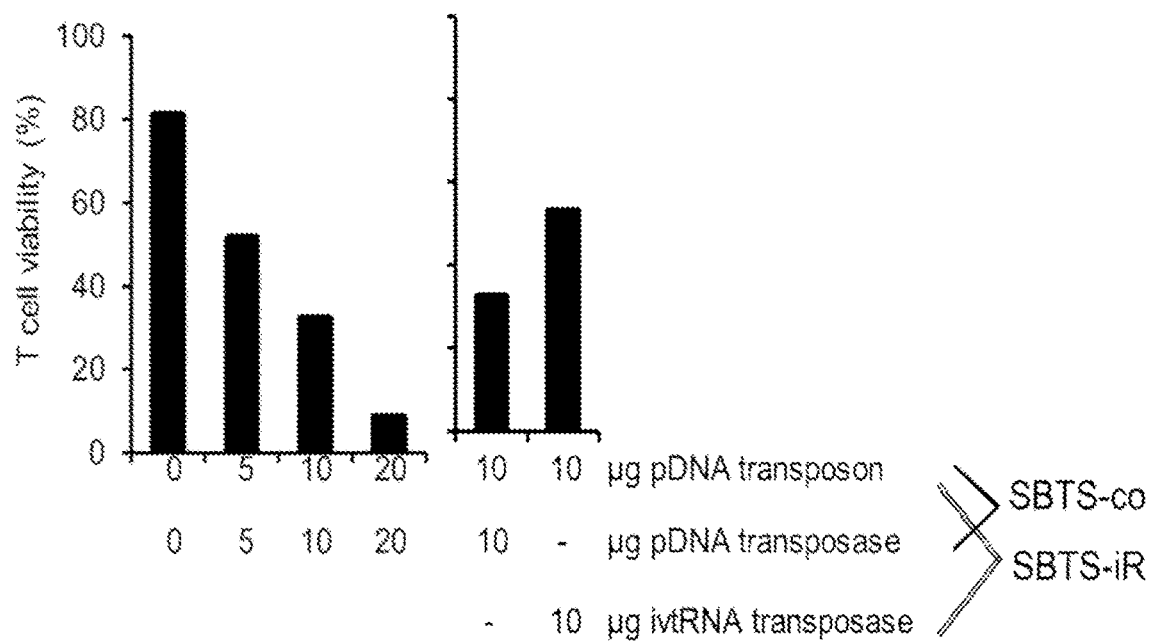

The inventors could show that use of the kit of the invention comprising ivtRNA encoding the transposase led to both high transfection efficiency, compared to DNA encoding transposase (FIG. 3) and improved viability (FIG. 4) of human T cells.

In an alternative embodiment, the nucleic acid encoding the transposase is DNA suitable for in vitro transcription. Preferably, in that embodiment, the kit also comprises reagents and, optionally, instructions, for in vitro transcription, such as ribonucleotide triphosphates containing 5' cap analogs, a buffer suitable for transcription, and an RNA polymerase suitable for in vitro transcription, e.g., T7 RNA polymerase. The DNA may be a vector for RNA production, e.g., pcDNA3.1+(hygro) (Thermo Fisher Scientific, Waltham, USA). The kit may comprise rabbit reticulocyte lysate, which comprises all reagents for in vitro transcription. Such a kit is to be used for producing ivtRNA, which is then, in accordance with the invention, used for preparing transfected cells, in particular transfected primary cells, preferably, primary T cells, or stem cells. Such cells are known to be especially hard to transfect.

The transposase encoded by the nucleic acid may be a transposase functional in vertebrate cells, in particular, in human cells. It is selected from the group of class II transposable elements comprising Sleeping Beauty transposase, FrogPrince, piggyBac, Tol2 and other Tc1/mariner-type transposases, preferably, Sleeping Beauty transposase, e.g., as disclosed in Ivics et al., 1997, most preferably, SB100X (Mátés et al., 2009).

The kit of the invention, as a second nucleic acid, further comprises minicircle DNA comprising the transposon, which can be mobilized by the transposase (FIG. 1C). In the context of the invention, the transposon does not encode a transposase itself. The transposon encodes a protein and/or a miRNA, wherein expression of the protein and/or the miRNA is regulated by a promoter. Minicircles are small circular plasmid derivatives that have been largely or completely freed from non-essential prokaryotic vector parts. In particular, minicircles do not contain DNA encoding for bacterial sequences like antibiotic resistance genes or the ORI.

The minicircle DNA of the invention preferably comprises less than 5 kb, more preferably, less than 4 kb, less than 3 kb or less than 2 kb. The inventors found that a minimal size of the DNA minicircle improves efficiency. The minicircle encodes an expression cassette comprising a promoter, an intron and a poly(A) signal as well as the TIR (terminal inverted repeats) of the transposon and a spacer, which altogether comprise about 1.75 kb. The final size of the minicircle depends on the size of the coding region.

Minicircles and their use in combination with Sleeping Beauty transposase are described in DE 10 2011 118 018 A1 or Garrets et al., 2016.

The inventors could show that use of the kit of the invention comprising mRNA encoding the transposase in combination with minicircle DNA comprising the transposon led to surprisingly both high transfection efficiency and cell viability (FIG. 5). This is of particular importance for the transfection of delicate or hard-to-transfect cells such as T cells, B cells, stem cells, and many other cell types, in particular, primary cells (FIG. 12).

The invention thus also provides a method for producing transfected cells, in particular transfected primary cells or stem cells, preferably, primary T cells such as primary human T cells, with high transfection efficiency and high viability. High or improved viability preferably is higher than 30%, more preferably, higher than 35% or higher than 40%. Viability may, e.g., be assessed on day 4 after transfection. High transfection efficiency preferably is higher than 50%, or more preferably, higher than 60% of viable cells. Said method comprises use of the kit of the invention. In particular, it comprises steps wherein the cells are contacted with a) mRNA encoding a transposase capable of mobilizing a transposon, preferably, Sleeping Beauty,
b) minicircle DNA comprising said transposon, wherein the transposon encodes at least one protein and/or at least one miRNA, wherein expression of the protein and/or the miRNA is regulated by a promoter. Preferably, the transposon encodes a protein and at least one, preferably, two miRNA, wherein expression of the protein and the miRNA is regulated by the same promoter.

Preferably, said contacting comprises electroporation.

Figure 6A:
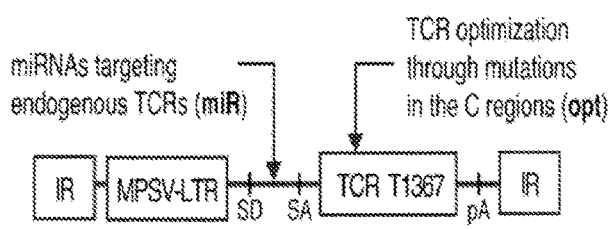
Figure 6B:
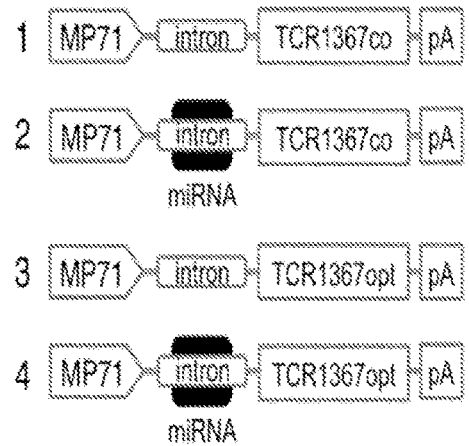

In a preferred embodiment of the invention, the transposon encodes a protein and a miRNA (FIG. 1D). Preferably, the transposon encoding a protein comprises an intron comprising sequences encoding the miRNA, wherein the expression of the protein and the miRNA is regulated by the same promoter (FIG. 6A). In a preferred embodiment, the transposon encoding a protein comprises an intron comprising sequences encoding at least two miRNAs, wherein the expression of the protein and the miRNAs is regulated by the same promoter.

The invention thus also provides a nucleic acid comprising a transposon, wherein the transposon encodes at least one protein and at least one miRNA, wherein the nucleic acid encoding the protein comprises an intron comprising sequences encoding the miRNA, wherein expression of the protein and the miRNA is regulated by the same promoter. The nucleic acid is selected from the group comprising a plasmid or minicircle DNA, preferably, a minicircle DNA. If the nucleic acid is not a minicircle DNA, it is suitable for generation of a minicircle DNA, as it comprises recombination sites outside the integration cassette which allow the production of a minicircle vector during propagation in a specific bacteria strain suitable for production of minicircles (Kay et al., 2010), e.g., ZYCY10P3S2T. (System Biosciences, Mountain View, USA). Such strains, e.g., are capable of expressing PhiC31 integrase and I-SceI endonucleoase. Said nucleic acid can, e.g., be an intermediate product in production of the kit of the invention.

A preferred intron employed in the transposon of the invention is a chimeric intron comprising a 5'-splice donor site from a first intron of a human β-globin gene and a 3'-splice acceptor site from an immunoglobulin gene heavy chain variable region, e.g., as disclosed in US20070190617. Preferable features of the intron are described in the data sheet for pCI and pSI mammalian expression vectors, Promega 7/09, and preferably, the intron comprised in said vectors is employed. Choi et al., 2014, Mol Brain 7:17 references the sequence of a vector comprising said intron.

In the state of the art, miRNAs are normally expressed from a different promoter, or placed 3' or 5' of the transgene. The incorporation of miRNA in introns has been shown to improve transgene expression (Chung et al., 2006). Notably, viral vectors do not allow the application of efficient introns. With the transposon of the invention, the inventors were able to silence several cellular factors of the target cells by incorporating multiple miRNAs and to gain high transgene expression levels at the same time. A similar gene silencing approach incorporated into gamma-retroviral vectors would result in decreased transgene expression levels.

An additional advantage of transposons versus viral vectors is that, according to the invention, in the context of transposons, two or more miRNA comprising the same miRNA backbone, and, e.g., even having the same complete miRNA sequence, can be used without compromising stability. This increases efficiency of downregulation of the target without requiring optimization of sequences (FIG. 8). In contrast, Amendola at al., 2009, showed that using the same miRNA twice in a viral vector led to instability and rearrangement of said vector. Thus, in a viral system, it is necessary to find a compromise between optimal efficiency of miRNAs, which depends on the interaction between miRNA backbone and target sequences, and the necessity to prevent recombination between identical or similar miRNA. In contrast, in the transposon system according to the invention, it is not necessary to find such compromises.

The invention further provides a nucleic acid comprising a transposon, wherein the transposon encodes at least one protein and two or more miRNA, preferably, three or more miRNA, four or more miRNA, five or more miRNA or six or more miRNA, wherein the nucleic acid encoding the protein comprises an intron comprising sequences encoding the miRNA, wherein expression of the protein and the miRNA is regulated by the same promoter. Optionally, of said miRNA, two or more miRNA, preferably, three or more miRNA, four or more miRNA, five or more miRNA or six or more miRNA, e.g, all miRNA, comprise the same backbone.

Preferably, for use in ATT, the protein encoded by the transposon is a TCR or CAR construct. The TCR construct may comprise one TCR alpha chain construct and one TCR beta chain construct, or a single chain TCR construct or a CAR construct. Preferably, the TCR construct comprises a TCR alpha chain construct and a TCR beta chain construct. Preferably, the CAR construct comprises a single chain variable fragment of an antibody (scFv) construct, a spacer region construct and a signaling region construct.

Optionally, codon usage of the TCR alpha chain construct and a TCR beta chain construct may be optimized to enhance expression of the TCR in recombinant T cells. Human variable regions may be combined with murine constant regions (Cohen et al., 2006), or a minimal murine constant region, i.e., human constant regions containing only defined amino acids from the murine constant region (Sommermeyer et al., 2010; Bialer et al., 2010) and additionally comprising an additional cysteine bridge (Cohen et al., 2007; Kuball et al., 2007), which increases preferential binding of transgenic TCR chains to each other and reduces pairing with endogenous TCR chains expressed by recipient T cells. The inventors have demonstrated that, optimally, the TCR construct comprises a TCR alpha chain and a TCR beta chain optimized for pairing with each other, wherein the TCR alpha and beta chain constructs preferably each comprise (a) additional Cys residues relative to native human TCRs and (b) murine amino acid sequences in the constant regions, wherein otherwise, the TCR chains are of human origin. In a preferred embodiment, the TCR construct comprises SEQ ID NO: 23.

Single chain (sc) TCR constructs are encompassed as well as heterodimeric TCR constructs. A scTCR can comprise a variable region of a first TCR chain construct (e.g., an alpha chain) and an entire (full-length) second TCR chain (e.g., a beta chain), or vice versa. Furthermore, the scTCR can optionally comprise one or more linkers, which join the two or more polypeptides together. The linker can be, for instance, a peptide, which joins together two single chains. A scTCR which is fused to a cytokine, e.g., a human cytokine, such as IL-2, IL-7, IL-15 or IL-21, can also be encoded.

Furthermore, soluble receptor molecules and fusion proteins may be generated containing the variable regions of the TCR alpha and TCR beta chain genes and e.g. antibody domains. These can be Ig domains, e.g., an IgG constant domain. Also, variable regions of the TCR chains may be fused to, e.g., anti-CD3 antibody domains in a fusion protein of the invention, e.g., to provide soluble monoclonal TCR reagents to target malignant cells expressing the respective peptide-major histocompatibility complex (pMHC) at the cell surface and engaging T cells via e.g. an anti-CD3 targeting domain to provide effector functions to the target cells (Liddy et al., 2012).

The TCR construct is capable of specifically binding to an antigen, preferably, an antigen specifically expressed or overexpressed by cancer cells and/or cells infected by a virus as well as cells involved in autoimmune diseases. The term "capable of specifically binding" or "recognizing" or "specific for" a given antigen, as used herein, means that a TCR construct can specifically bind to and immunologically recognize an epitope, preferably with high affinity and through its variable domains. Affinity can be analyzed by methods well known to the skilled person, e.g. by BiaCore.

In a preferred embodiment, the transposon further encodes at least two miRNAs, optionally, three, four, five, six, seven, eight, nine, ten or more miRNAs (FIG. 6A, B). In combination with the encoded protein being a TCR construct or CAR construct, it is preferred that the miRNA encoded by the transposon is capable of suppressing the expression of a TCR alpha and/or TCR beta chain, in particular, both endogenous TCR chains of the T cell. Mispairing of TCR chains is thus prevented. Expression of the encoded protein, however, is not silenced, in particular, the miRNA is not capable of silencing expression of the TCR chain or TCR construct or CAR encoded by the transposon. Preferably, the TCR chain or TCR construct encoded by the transposon is codon-optimized and the sequence thus differs significantly from the endogenous TCR sequences. Embodiments wherein the miRNA encoded by the transposon is capable of suppressing the expression of a TCR alpha and/or TCR beta chain, in particular, both endogenous TCR chains of the T cell can also be of interest, e.g., for prevention of GvHD (graft-versus-host disease) or reduction of GvHD (cf. U.S. Pat. No. 9,181,527).

Figure 6C:
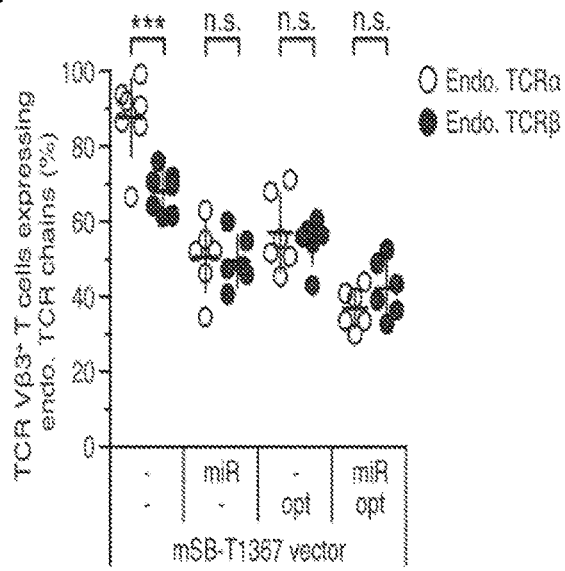
Figure 6D:
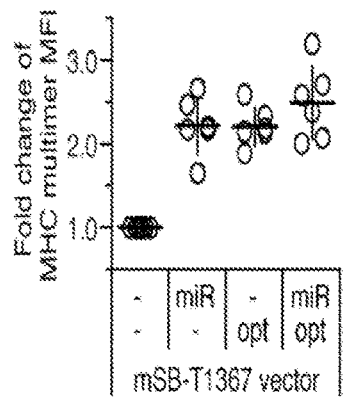

The inventors were able to show that the minicircle DNA transposon constructs of the invention are suitable for co-expression of a transgene and even multiple miRNAs, without abrogating the expression of the transgene. Suppression of endogenous TCR expression reduces generation of potentially dangerous mixed TCRs that are composed of one endogenous and one transgenic TCR chain. Also, silencing of the endogenous TCR (FIG. 6C) facilitates expression of the transgenic, therapeutic TCR that requires cellular co-factors for surface expression. Thus, the transposon-based vector of the invention provides for both an efficient expression of functional TCR (FIG. 6D, FIG. 7A, B) and a crucial safety feature.

The transposon preferably encodes two miRNAs capable of silencing expression of a TCR alpha chain and TCR beta chain. The miRNAs are typically capable of silencing the expression of the endogenous TCR chains of the T cell, which is to be genetically modified. Suitable exemplary sequences encoding miRNAs are provided in SEQ ID NO: 15 and SEQ ID NO: 16, or in SEQ ID NO: 19.

In one embodiment, the transposon encodes two or more, preferably, two miRNA having the same backbone sequences, or two or more miRNA having the same sequence.

Alternatively or additionally, a miRNA encoded by the transposon is capable of silencing expression of a protein capable of limiting the therapeutic efficiency of the transferred cells. In case of immunotherapy of cancer or virus-associated disease the protein capable of downregulating effector functions and/or proliferation of a T cell is selected from the group of inhibitory surface receptors comprising CTLA4, PDCD1, LAG3, HAVCR2 and TIGIT, from the group of intracellular proteins that negatively regulate TCR or costimulatory pathways comprising CBLB, CISH, DGK and TNFAIP3, from the group of intracellular proteins that limit cytokine production comprising SPRY2 and CREM or from the group of proteins stabilizing a dysfunctional T cell phenotype comprising MAF, EGR3, NDRG1 and DTX1.

In the context of ATT, the promoter, which regulates expression of the protein and/or the miRNA(s) is functional for expression in a T cell. Preferably, MPSV promoter may be used for T cell engineering. Alternative promoters are EF1a, PGK, CMV, CAG and others.

In one embodiment, the invention provides pSB-miR-T1367 (SEQ ID NO: 22), or the parental plasmid for generation of a minicircle of the invention according to SEQ ID NO:14. Of course, the plasmid or minicircle may alternatively encode a different TCR construct.

In a preferred embodiment, throughout the invention, the transposon comprises a cargo nucleic acid flanked by a left and a right inverted repeat/direct repeat (IR/DR), wherein
(i) the transposon is capable of being mobilized by a Sleeping Beauty transposase protein;
(ii) the left IR/DR comprises an outer left DR motif and an inner left DR motif, wherein the outer left DR motif comprises the nucleotide sequence of SEQ ID NO:1 and the inner left DR motif comprises the nucleotide sequence of SEQ ID NO: 2; and
(iii) the right IR/DR comprises an outer right DR motif and an inner right DR motif, wherein the outer right DR motif comprises an inverted sequence of the nucleotide sequence of SEQ ID NO:1 and the inner right DR motif comprises an inverted sequence of the nucleotide sequence of SEQ ID NO: 2.

The cargo nucleic acid comprises the at least one protein and at least one miRNA of the invention. Preferably, said outer left DR motif comprises the nucleotide sequence of SEQ ID NO:3 and/or said outer right DR motif comprises an inverted sequence of the nucleotide sequence of SEQ ID NO:4. Preferably, the inner left DR motif comprises the nucleotide sequence of SEQ ID NO: 5 and/or the inner right DR motif comprises an inverted sequence of the nucleotide sequence of SEQ ID NO: 6. Preferably, the left IR/DR comprises a HDR region capable of functioning as an enhancer comprising the nucleotide sequence of SEQ ID NO:7 between the outer DR and inner DR, wherein, optionally, the right IR/DR also comprises reverse complement of said HDR region. Preferably, the left IR/DR comprises the nucleotide sequence selected from the group consisting of SEQ ID NO: 8 and SEQ ID NO: 9. Preferably, the right IR/DR comprises the reverse complement nucleotide sequence selected from the group consisting of SEQ ID NO: 10, SEQ ID NO:11, SEQ ID NO: 12 and SEQ ID NO: 13. It was shown that such transposons, designated pT4 or pT5 transposons, have high efficiencies of transposition, and can thus be advantageously used in the context of the present invention.

TABLE 1

Preferred IR/DR sequences

Left IR/DR of pT4 with HDR:

| | | |
|---|---|---|
| Left outer DR | SEQ ID NO: 1 | CAGTTGAAGT CGGAAGTTTA CATACACYTW AG |
| Left inner DR | SEQ ID NO: 2 | YCCAGTGGGT CAGAAGTGTA CATACAC<u>GVK</u> <u>CT</u> |
| HDR | SEQ ID NO: 7 | GTKTA CAKACASD |
| Framework: | | pT |

SEQ ID NO: 8
TACAGTTGAAGTCGGAAGTTTACATACACYTWAGTTGGAGTCATT
AAAACTCGTTTTTCAACTACTCCACAAATTTCTTGTTAACAAACA
ATAGTTTTGGCAAGTCAGTTAGGACATCTACTTTGTGCATGACAC
AAGTCATTTTTCCAACAATT<u>GTKTACAKACASD</u>TTATTTCACTTA
TAATTCACTGTATCACAAT<u>YCCAGTGGGTCAGAAGTGTACATACA</u>
<u>CGVKCT</u>

Left IR/DR of pT5 with HDR:

| | | |
|---|---|---|
| Left outer DR | SEQ ID NO: 1 | CAGTTGAAGT CGGAAGTTTA CATACACYTW AG |
| Left inner DR | SEQ ID NO: 2 | YCCAGTGGGT CAGAAGTGTA CATACAC<u>GVK</u> <u>CT</u> |
| HDR | SEQ ID NO: 7 | GTKTA CAKACASD |
| Framework: | | pT2 |

SEQ ID NO: 9
TATACAGTTGAAGTCGGAAGTTTACATACACYTWAGTTGGAGTCA
TTAAAACTCGTTTTTCAACTACTCCACAAATTTCTTGTTAACAAA
CAATAGTTTTGGCAAGTCAGTTAGGACATCTACTTTGTGCATGAC
ACAAGTCATTTTTCCAACAATT<u>GTKTACAKACASD</u>TTATTTCACT
TATAATTCACTGTATCACAAT<u>YCCAGTGGGTCAGAAGTGTACATA</u>
<u>CACGVKCT</u>

Right IR/DR of pT4 without HDR (right IR/DR comprises the reverse complement of the given sequences):

| | | |
|---|---|---|
| Right outer DR | SEQ ID NO: 1 | CAGTTGAAGT CGGAAGTTTA CATACACYTW AG |
| Right inner DR | SEQ ID NO: 2 | YCCAGTGGGT CAGAAGTGTA CATACAC<u>GVK</u> <u>CT</u> |
| Framework: | | pT |

SEQ ID NO: 10
TACAGTTGAAGTCGGAAGTTTACATACACYTWAGCCAAATACATT
TAAACTCACTTTTTCACAATTCCTGACATTTAATCCGAGTAAAGA
TTCCCTGTCTTAAGGTCAGTTAGGATCACCACTTTATTTTAAGAA
TGTGAAATATCAGAATAATAGTAGAGAGAATGATTCATTTCAGCT
TTTATTTCTTTCATCACATT<u>YCCAGTGGGTCAGAAGTGTACATAC</u>
<u>ACGVKCT</u>

Right IR/DR of pT5 without HDR (right IR/DR comprises the reverse complement of the given sequences):

| | | |
|---|---|---|
| Right outer DR | SEQ ID NO: 1 | CAGTTGAAGT CGGAAGTTTA CATACACYTW AG |
| Right inner DR | SEQ ID NO: 2 | YCCAGTGGGT CAGAAGTGTA CATACAC<u>GVK</u> <u>CT</u> |
| Framework: | | pT2 |

SEQ ID NO: 11
TATA<u>CAGTTGAAGTCGGAAGTTTACATACACYTW</u>AGCCAAATACA
TTTAAACTCACTTTTTCACAATTCCTGACATTTAATCCTAGTAAA
AATTCCCTGTCTTAGGTCAGTTAGGATCACCACTTTATTTTAAGA

TABLE 1-continued

Preferred IR/DR sequences

ATGTGAAATATCAGAATAATAGTAGAGAGAATGATTCATTTCAGC
TTTTATTTCTTTCATCACATTYCCAGTGGGTCAGAAGTGTACATA
CACGVKCT

Right IR/DR of pT4 with HDR (right IR/DR
comprises the reverse complement of the given
sequences):

| | | |
|---|---|---|
| Right outer DR | SEQ ID NO: 1 | CAGTTGAAGT CGGAAGTTTA CATACACYTW AG |
| Right inner DR | SEQ ID NO: 2 | YCCAGTGGGT CAGAAGTGTA CATACACGVK CT |
| HDR | SEQ ID NO: 7 | GTKTA CAKACASD |
| Framework: | | pT |

SEQ ID NO: 12
TACAGTTGAAGTCGGAAGTTTACATACACYTWAGCCAAATACATT
TAAACTCACTTTTTCACAATTCCTGACATTTAATCCGAGTAAAGA
TTCCCTGTCTTAAGGTCAGTTAGGATCACCACTTTATTTTAAGAA
TGTGAAATATCAGAATAATAGTAGAGAGAATGATGTKTACAKACA
SDTCATTTCAGCTTTTATTTCTTTCATCACATTYCCAGTGGGTCA
GAAGTGTACATACACGVKCT

Right IR/DR of pT5 with HDR (right IR/DR
comprises the reverse complement of the given
sequences):

| | | |
|---|---|---|
| Right outer DR | SEQ ID NO: 1 | CAGTTGAAGT CGGAAGTTTA CATACACYTW AG |
| Right inner DR | SEQ ID NO: 2 | YCCAGTGGGT CAGAAGTGTA CATACACGVK CT |
| HDR | SEQ ID NO: 7 | GTKTA CAKACASD |
| Framework: | | pT2 |

SEQ ID NO: 13
TATACAGTTGAAGTCGGAAGTTTACATACACYTWAGCCAAATACA
TTTAAACTCACTTTTTCACAATTCCTGACATTTAATCCTAGTAAA
AATTCCCTGTCTTAGGTCAGTTAGGATCACCACTTTATTTTAAGA
ATGTGAAATATCAGAATAATAGTAGAGAGAATGATGTKTACAKAC
ASDTCATTTCAGCTTTTATTTCTTTCATCACATTYCCAGTGGGTC
AGAAGTGTACATACACGVKCT

Y = C/T, wherein Y preferably is T in the left DRs and C in the right DRs;
W = A/T, wherein W preferably is A in the left DRs and T in the right DRs;
V = A/G/C, wherein V preferably is C;
K = G/T, wherein K preferably is G;
S = C/G,
D = A/T/G.
Most preferably, Y is T in the left DRs and C in the right DRs; W is A in the left DRs and T in the right DRs; V is C; S is C, D is G and K is G.

In a preferred embodiment of the transposon, the left IR/DR comprises the nucleotide sequence of SEQ ID NO: 8 and the right IR/DR comprises the reverse complement nucleotide sequence of SEQ ID NO: 10 or SEQ ID NO:12. In these polynucleotides, the framework region corresponds to pT, and the polynucleotide of the invention is designated pT4.

In another preferred embodiment of the transposon, the left IR/DR comprises the nucleotide sequence of SEQ ID NO: 9 and the right IR/DR comprises the reverse complement nucleotide sequence of SEQ ID NO: 11 or SEQ ID NO:13. In these polynucleotides, the framework region corresponds to pT2, and the polynucleotide of the invention is designated pT5.

The minicircle DNA comprising the transposon, e.g., as described above and in the examples, is preferably comprised in the kit of the present invention.

The present invention also comprises a method for preparing transfected cells, wherein the cells which are transfected preferably are primary cells, most preferably primary T cells, the method comprising transfecting cells with the nucleic acids of the kit of the invention, the nucleic acids comprising a) mRNA encoding a transposase capable of mobilizing a transposon; and b) minicircle DNA comprising said transposon, wherein the transposon encodes a protein and/or a miRNA, wherein expression of the protein and/or the miRNA is regulated by one promoter.

Preferably, the cells are transfected by electroporation, however, other non-viral transfection methods are also possible, e.g., physical methods such as cell squeezing, sonoporation, hydrodynamic delivery, chemical-based transfection methods with calcium phosphate, dendrimers, liposomes or cationic polymers, or particle-based methods such as with a gene gun.

In the method of the invention, preferably, the cells, which are transfected, e.g., electroporated, are primary human T cells isolated from a patient. In that case, the method optionally further comprises stimulating the T cells with one or more stimulants selected from the group comprising anti-CD3 antibodies, anti-CD28 antibodies, anti-CD137 antibodies, anti-CD134 antibodies, anti-CD357 antibodies, IL-2, IL-7, IL-15, and IL-21. However, the inventors could show that, in the method of the invention, even without such a stimulus, the transfected T cells survive and can be expanded.

In one embodiment, the method of the invention does not comprise selection and/or enrichment of the transfected cells.

The method of the invention thus also constitutes a method for preparing transfected cells having an enhanced viability. Using a preferred transposon of the invention encoding a TCR construct and miRNAs capable of downregulating expression of endogenous TCR chains, the method of the invention is particularly suitable for preparing transfected TCR transgenic cells having a reduced expression of endogenous TCR chains, and/or for reducing pairing of transgenic and endogenous TCR chains.

Using the kit and method of the invention, T cells specific for an epitope from a defined antigen presented on a major histocompatibility complex (MHC) may be generated by expressing the nucleic acids encoding the TCR construct. If such T cells are intended for therapy of a patient, it is preferred to use autologous T cells. Alternatively, an allogeneic setting is possible, using immune suppression.

The invention also provides a population of genetically modified cells, e.g., T cells, comprising the transposon described above or in the examples which encodes at least one protein and at least one miRNA, wherein the nucleic acid encoding the protein comprises an intron comprising sequences encoding the miRNA, wherein expression of the protein and the miRNA is regulated by the same promoter. Said population of genetically modified cells is preferably obtainable by the method of the invention.

The invention also provides a pharmaceutical composition comprising a population of genetically modified cells as described above, e.g., comprising the transposon described above or in the examples which encodes at least one protein and at least one miRNA, wherein the nucleic acid encoding the protein comprises an intron comprising sequences encoding the miRNA, wherein expression of the protein and the miRNA is regulated by the same promoter. Preferably, said pharmaceutical composition is for use in treating a patient by adoptive T cell therapy, wherein the patient is selected from the group comprising cancer patients and/or patients infected with a viral or bacterial pathogen and/or patients with autoimmune diseases, and wherein the cells comprise T cells expressing a TCR or CAR construct, and, preferably, miRNA suppressing expression of the T cells endogenous TCR. The pharmaceutical composition may be for use in prevention of infection or in reducing infection with a pathogen such as a virus, e.g., CMV, EBV, HIV or HPV, wherein suitable TCR or CAR constructs are employed.

The invention also teaches a method of treatment of a patient in need thereof (e.g., infected with a virus, or suffering from cancer, e.g., cancer associated with a virus, e.g., suffering from an autoimmune disease), or of reducing infection with a virus, or symptoms of said infection, comprising administering to said patient a suitable pharmaceutical composition of the invention.

Throughout the invention, the T cells may be CD8+ or CD4+ T cells, preferably CD8+ cells or regulatory T cells. Pharmaceutical compositions may also comprise both transgenic CD4+ and CD8+ T cells, wherein the respective TCRs are preferably directed to different epitopes of the same antigen. Preferably, the T cells are human T cells, and the patient to be treated is a human patient.

The invention is further illustrated by the examples below, which are intended to exemplify the invention, and not to limit its scope. All references cited herein are herewith fully incorporated. All embodiments of the invention disclosed herein can be combined.

FIGURES

FIG. 1

Schematic overview of improvements of the Sleeping Beauty transposon-based gene transfer system applied in the invention.

In comparison to the conventional Sleeping Beauty transfer system (A) the kit of the invention includes a mRNA (ivtRNA) encoding the Sleeping Beauty transposase (B), minicircle DNA comprising the transposon encoding the transgene (C) and miRNAs silencing endogenous genes, which hamper efficient transgene, e.g. TCR, expression and therapeutic efficacy (D).

FIGS. 2A and 2B

Transfection of plasmid DNA into human T cells leads to dose-dependent T cell mortality.

Human T cells transfected with GFP-encoding plasmid DNA (pSB-GFP) revealed a dose-dependent mortality while similar amounts of transfected GFP-mRNA showed only a slight reduction in T cell counts (2A). Transfection of GFP-ivtRNA is more efficient and results in more GFP T cells compared to transfection of pSB-GFP. Furthermore, the transfection of high DNA amounts (>10 µg) results in a decrease of GFP T cells three to four days after transfection (2B).

FIG. 3

Transposase delivered as ivtRNA and as transposase encoding plasmids yield similar gene transfer efficiency.

Comparison of GFP expression in human T cells using the conventional Sleeping Beauty transposon-based gene transfer system delivering the transposase as DNA plasmid (SBTS-co) and the Sleeping Beauty transposon-based gene transfer system of the invention delivering the transposase as ivtRNA (SBTS-iR). Shown is the percentage of GFP+CD3+ T cells at day 1 (transient expression) and day 12 (stable expression).

FIG. 4

Sleeping Beauty transposon-based gene transfer delivering the transposase as ivtRNA increases cell viability.

SBTS-co and SBTS-iR, as sown in FIG. 2, are employed to transfect human T cells with a GFP-encoding transposon. Shown is the percentage of viable T cells 24 hrs after transfection using different amounts of transposon plasmid and either DNA transposase or ivtRNA transposase.

FIGS. 5A, 5B, and 5C

Sleeping Beauty transposon-based gene transfer using a minicircle DNA transposon increases transfection efficiency.

Comparison of Sleeping Beauty transposon-based gene transfer system containing transposase encoding ivtRNA and either transposon plasmid DNA (pSB) or transposon minicircle DNA (mSB), both encoding GFP (5A). Shown are the Mean Fluorescence Intensity, MFI (5B) and the percentage of GFP+ human T cells (5C). pmax-GFP represents a transient transfection control without ivtRNA transposase, non-TF represents transfection conditions without employing nucleic acids.

FIGS. 6A, 6B, 6C, and 6D

Sleeping Beauty transposon-based gene transfer system delivering a minicircle transposon DNA encoding an engineered TCR and miRNA for endogenous TCR silencing results in improved expression of the therapeutic TCR.

Minicircle transposon vector harboring miRNAs (miR) and modifications in the MAGE-A1-reactive TCR T1367 sequence (6A). Minicircle transposon vectors containing the TCR T1367 with different modifications. 1: TCR codon-optimized; 2: as 1 plus miRNA cassette (miR); 3 TCR codon-optimized, additional cysteine bond, minimal murinized C-regions (opt); 4 as 3 plus miRNA cassette (miR opt) (6B). Expression of miRNA decreases the formation of mispaired TCRs formed between therapeutic and endogenous TCR chains (6C). Expression of miRNA increases the functionality of TCR-engineered human T cells as measured by MHC multimer binding (6D).

Figure 7A:
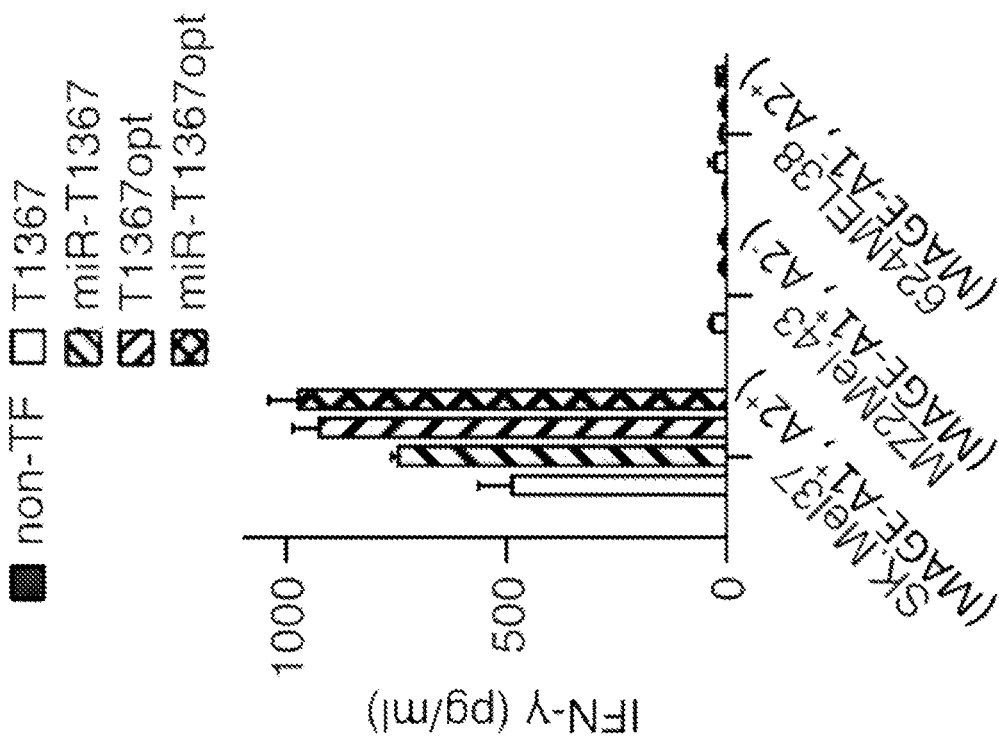
Figure 7B:
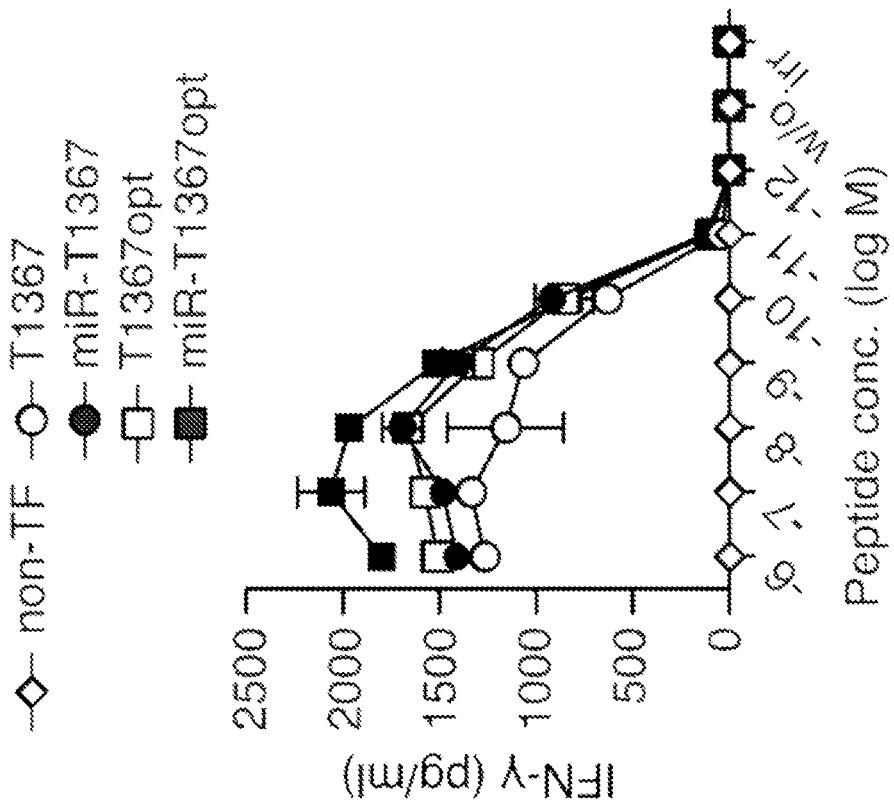

FIGS. 7A and 7B

Human T cells engineered with a fully optimized Sleeping Beauty transposon-based gene transfer system show improved functionality.

Human T cells were transfected with the fully optimized Sleeping Beauty transposon-based gene transfer system (ivtRNA encoding the transposase, minicircle transposon DNA containing a miRNA to knockdown the expression of endogenous TCRs, optimized therapeutic TCR) and show improved IFN-γ release in response to peptide-loaded indicator cells (7A) and a MAGE-A1+11 LA-A*02:01+ (MAGE-A1+, A2+) tumor cell line while A2− and MAGE-A1− cell lines are not recognized (7B).

Figure 8A:
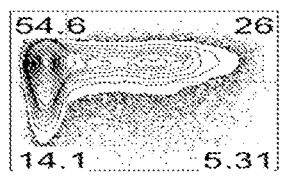
Figure 8B:
Figure 8C:

FIGS. 8A, 8B, and 8C

Combination of identical miRNAs in one vector (2× same miRNA) is possible with the system of the invention.

Jurkat cells were electroporated with transposase plasmid and SB transposon plasmids encoding for GFP and one (8B) or two identical (8C) miRNAs specific for the human TCR alpha chain (TRAC, SEQ ID NO: 15) or without miRNA (8A) and analyzed by flow cytometry for CD3 surface expression after 8 days. Knockdown rates were 74% with one miRNA cassette and 84% with the same miRNA cassette incorporated twice into the transposon vector.

Figure 9A:
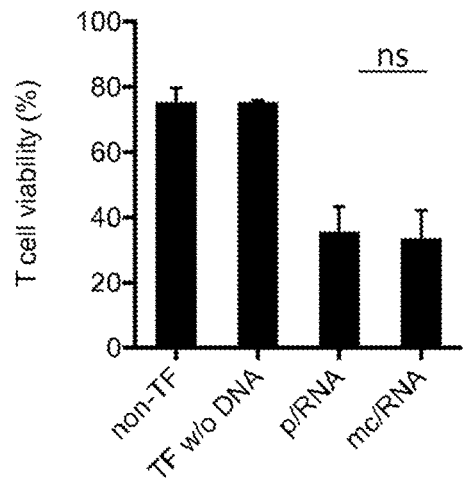
Figure 9B:
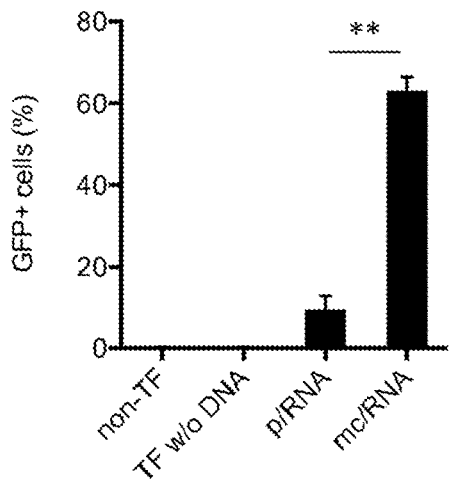

FIGS. 9A and 9B

Primary human T cells (HTC): plasmid (p) vs. minicircle (mc).

Primary human T cells were electroporated with 15 μg SB transposase RNA and 2.5 μg SB transposon vector as either plasmid or minicircle and analyzed by flow cytometry after 4 days. Providing SB transposons as minicircles instead of conventional plasmids substantially increased transfection efficiency (9B) without compromising T cell viability (9A).

Figure 10A:
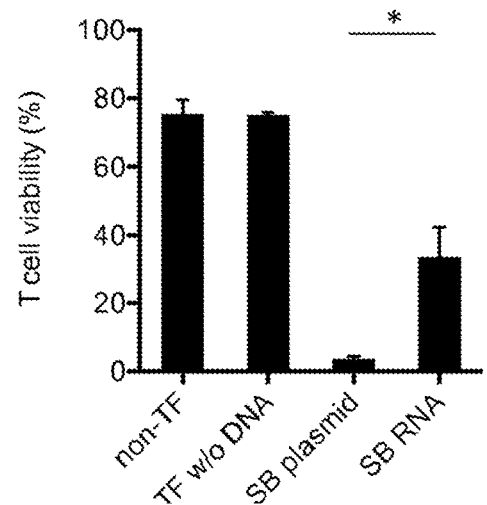
Figure 10B:
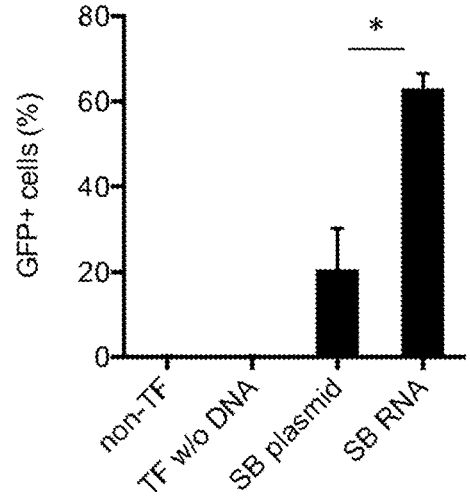

FIGS. 10A and 10B

Primary human T cells (HTC): SB RNA vs. SB plasmid.

Primary human T cells were electroporated with 2.5 μg SB transposon minicircles encoding for GFP and 15 μg SB transposase as in vitro transcribed RNA (SB RNA) or as plasmid (SB plasmid) and analyzed by flow cytometry after 4 days. Providing SB transposase as RNA instead of plasmid DNA reduces T cell mortality after transfection, i.e., T cell viability is increased (10A). It also increased transfection efficiency (10B).

Figure 11A:
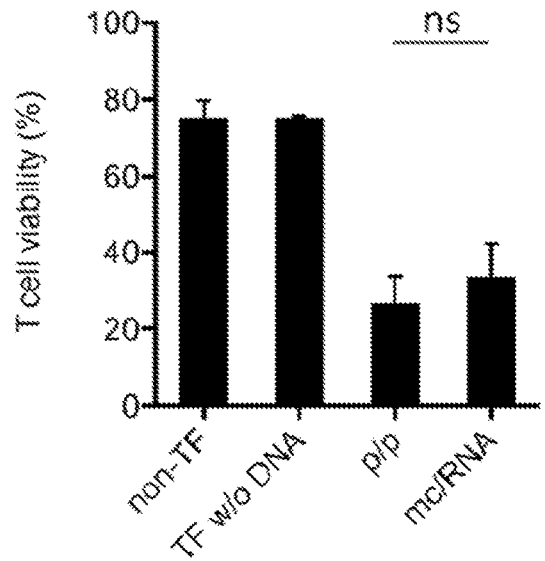
Figure 11B:
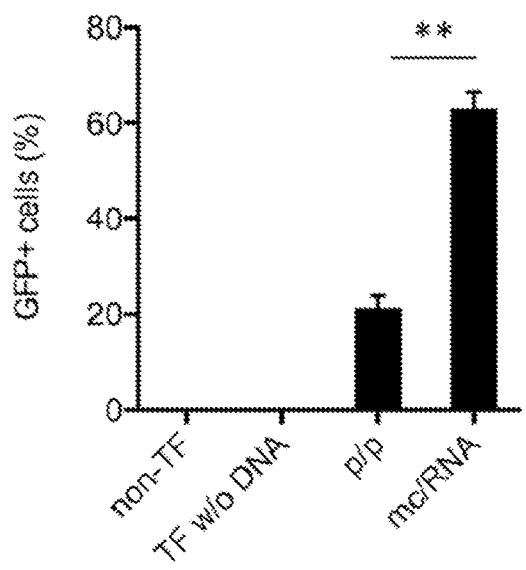

FIGS. 11A and 11B

Primary human T cells (HTC): conventional two plasmid (p) system vs. minicircle (mc)/RNA.

Primary human T cells were electroporated either with the conventional SB two plasmid system using 2.5 μg transposon vector and 2.5 μg transposase vector or with 2.5 μg transposon minicircle and 15 μg SB RNA and analyzed by flow cytometry after 4 days. The application of minicircles and RNA instead of the conventional two plasmid system substantially increased transfection efficiency (11B) without compromising T cell viability (11A).

Figure 12A:
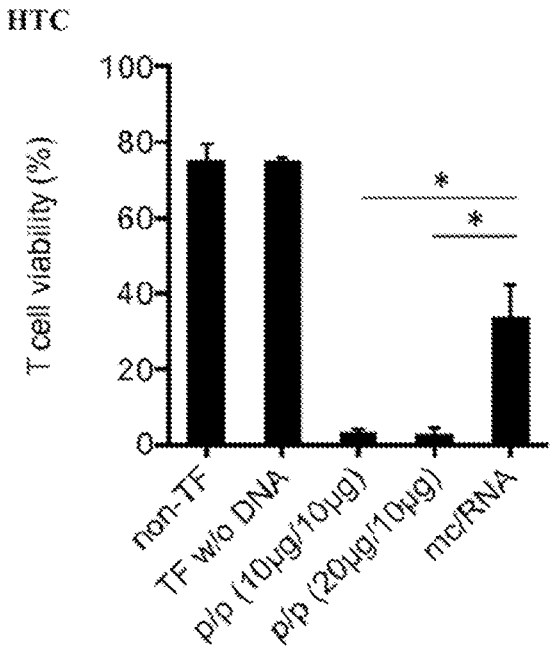
Figure 12B:
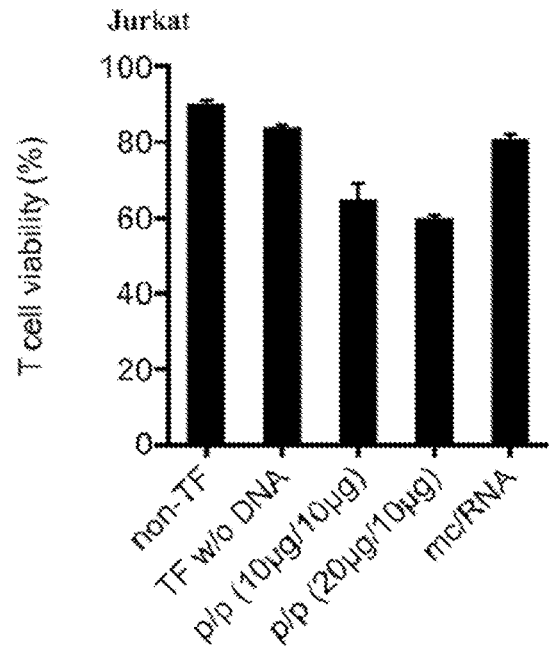

FIGS. 12A and 12B

Comparison of Jurkat cells and Primary human T cells (HTC): conventional two plasmid (p) system vs. minicircle (mc)/RNA.

Alternative approaches use large amounts of plasmid DNA to achieve similar efficiencies. However, usage of these large amounts of plasmid DNA leads to high cell mortality impeding large scale generation of T cells for clinical application. Whereas this approach works for the transfection of cell lines, primary T cells rarely survive transfection with large amounts of DNA. Furthermore, DNA-transfected primary T cells show a delay in T cell activation and hence are hard to expand. Here, we compare our approach using transposon minicircles and transposase RNA with conventional approaches using large amounts of plasmid DNA. Primary human T cells (12A) or Jurkat cell line cells (12B) were electroporated with the conventional SB two plasmid system using large amounts of DNA (10 μg/10 μg or 20 μg/10 μg) that have been reported to achieve high transfection efficiency, or with our minicircle/RNA approach and analyzed by flow cytometry after 4 days. Whereas Jurkat cells tolerate large amounts of DNA, primary T cells hardly survive the application of 20 μg or 30 μg of total DNA. Our minicircle/RNA approach, however, enables efficient transfection of primary T cells ensuring viable T cells after electroporation (30-40% viability).

EXAMPLES

Example 1

Production of Conventional Sleeping Beauty Gene Transfer System (SBTS-Co)

The Sleeping Beauty pT2/HB transposon plasmid (Cui et al., 2002) was modified to carry the MPSV promoter of the MP71 retroviral vector (Engels et al., 2003), a chimeric intron, and the polyA signal of psiCHECK2 (Promega, Madison, USA). The enhanced green fluorescent protein (GFP) and the MAGE-A1-specific human TCR T1367 transgene (Obenaus et al., 2015), respectively, was then cloned into the modified pT2 vector to obtain pSB-GFP and pSB-T1367, respectively.

For efficient TCR expression, the TCR T1367 sequence was codon-optimized (Geneart, Darmstadt, Germany) and the TCRα- and TCRβ-chain were linked via the 2A element of porcine teschovirus (P2A) by PCR (Leisegang et al., 2008). TCR T1367 human constant regions were replaced by minimally murinized counterparts (Sommermeyer and Uckert, 2010) containing an additional cysteine bridge (Kuball et al., 2007; Rosenberg et al., 2008), (T1367opt). The final TCR construct corresponds to SEQ ID NO: 23 (Patent WO2014118236 A2, High avidity antigen recognizing constructs). Transposon plasmid DNA (pSB-GFP, pSB-T1367) was produced using EndoFree Plasmid Maxi Kit (Qiagen, Hilden, Germany). The transposon plasmids were used in conjunction with the Sleeping Beauty SB100X transposase (Mátés et al., 2009), which was delivered as DNA plasmid, to transfect human T cells by electroporation.

Example 2

Production of the Sleeping Beauty Gene Transfer System Using In Vitro Transcribed (ivt)RNA Transposase (SBTS-iR)

ivtRNA encoding the Sleeping Beauty SB100X transposase or GFP was prepared from pcDNA3.1/Hygro(+) (Invitrogen, Carlsbad, USA) using mMESSAGE mMACHINE T7 kit (ThermoFischer, Waltham, USA) according to the manufacturer's instruction. A poly(A)-tail was added using Poly(A)-tailing kit (ThermoFischer, Waltham, USA) and RNA was purified on columns with RNeasy Kit (Qiagen). ivtRNA transposase was used in conjunction with the modified Sleeping Beauty pT2/HB transposon plasmids (Example 1) to transfect human T cells by electroporation.

Example 3

Production of Sleeping Beauty Transposon Minicircle DNA

For the generation of parental minicircle vectors the cassette containing the promoter, intron, transgene and polyA signal was inserted into the plasmid pMC.BESPX-MCS2 (System Biosciences, Mountain View, USA) via the BamHI restriction site. A 210 bp spacer was inserted between the minicircle recombination site attB and the left inverted repeat. The final plasmid corresponds to SEQ ID NO: 14. Sleeping Beauty transposon minicircle DNA (mSB-GFP, mSB-T1367) was produced using the MC-Easy Minicircle DNA Production kit (System Biosciences, Palo Alto, USA) and EndoFree Plasmid Mega Kit (Qiagen) according to the manufacturers' instruction. A poly(A)-tail was added using Poly(A)-tailing kit (ThermoFischer) and RNA was purified on columns with RNeasy Kit (Qiagen). Transposon minicircle DNA was used in conjunction with ivtRNA transposase (Example 2) to transfect human T cells by electroporation.

Example 4

Production of Micro (mi)RNA for Silencing of Endogenous TCRs

The human TCR-specific miRNA cassettes were designed as described by us for mouse TCRs (Bunse et al., 2014). The TCRα-specific antisense sequence TGA AAG TTT AGG TTC GTA TCT G (SEQ ID NO: 15) and the TCRβ-specific antisense sequence TCT GAT GGC TCA AAC ACA GCG A (SEQ ID NO: 16) were integrated into the miRNA environments miR-155 (Chung et al., 2006), SEQ ID NO:17 and an artificial miRNA (Særom et al., 2006), SEQ ID NO: 18, respectively, obtaining SEQ ID NO: 19.

The miRNAs were then inserted into the intron of the TCR transposon plasmid to obtain pSB-miR-T1367co (SEQ ID NO: 22).

Example 5

Isolation and Electroporation of T Cells and Electroporation of Jurkat Cells

T cells were prepared from freshly isolated PBMC by centrifugation on Biocoll (Biochrom, Berlin, Germany) and subsequent enrichment using EasySep Human T Cell Enrichment Kit (STEMCELL Technologies, Köln, Germany). In case of TCR transfer, Vβ3-positive cells were depleted from the cell fraction by incubation with a PE-labeled anti-Vβ3 antibody (clone Jovi-3, Ancell, Bayport, USA) and subsequent selection with anti-PE beads (STEMCELL Technologies, Vancouver, Kanada). Electroporation was performed with Amaxa human T cell Nucleofector Kit (Lonza, Basel, Schweiz) for T cells and with Amaxa Cell Line Nucleofector Kit V for Jurkat cells according to the manufacturer's instruction. 6-10×10$^6$ T cells or 5-10×10$^6$ Jurkat cells were suspended in 100 µl nucleofection buffer and 1.25 µg to 20 µg transposon vector DNA and transferred into a cuvette. Then, program U-14 was applied for T cells, program X-01 for Jurkat cells, cells were immediately supplied with 2 ml T cell medium (TCM: RPMI 1640, 10% fetal calf serum, 1 mM sodium pyruvate, 1× non-essential amino acids) and cultured overnight. One day after electroporation, T cells were resuspended in 2 ml fresh TCM supplemented with 400 U/ml recombinant human interleukin-2 (IL-2, Chiron, Marburg, Germany) and activated by seeding them on 24-well plates coated with anti-CD3 (clone OKT3, 5 µg/ml) and anti-CD28 (clone CD28.2, 1 µg/ml) antibodies. Cells were then expanded for up to 18 days. Three to four days prior to functional analysis the concentration of IL-2 was reduced to 40 U/ml.

Example 6

Analytical Measurements:
Flow Cytometry

T cell surface stainings were performed in 50 µl PBS for 30 min at 4° C. with mAbs directed against CD8 (HIT8α), Vβ3 (Jovi-3, Ancell), CD25 (BC96), CD28 and CD3 (UCHT1). Antibodies were purchased from Biolegend (San Diego, USA), eBioscience, BD or Beckman Coulter. MAGE-A1/HLA-A2 multimer (MBL International, Woburn, USA) staining was performed for 30 min at 4° C. T cell viability was determined by dead cell staining with SYTOX Blue (Life Technologies, Carlsbad, USA) and a FSC/SSC lymphocyte gate. Data were acquired on FACS CantoII (BD) or MACS Quant (Miltenyi Biotec, Bergisch Gladbach, Germany) and analyzed with FlowJo software (Tree Star, Ashland, USA). The MAGE-A1$_{278}$-specific peptide (KVLEYVIKV, SEQ ID NO: 20) and the irrelevant tyrosinase-specific control peptide Tyr$_{369}$ (YMDGTMSQV, SEQ ID NO: 21) were generated by Biosyntan (Berlin, Germany).

Cytokine Release Assay

For detection of secreted cytokines, TCR-modified T cells were seeded in 96-well round-bottom plates (10$^4$ per well) together with either MAGE-A1$_{278}$-loaded T2 cells or tumor cell lines in an effector:target (E:T) ratio of 1:1. Supernatants were harvested after 24 h and either analyzed by ELISA or cytometric bead array (both BD).

REFERENCES

Amendola at al., Regulated and multiple miRNA and siRNA delivery into primary cells by a lentiviral platform. Mol. Therapy 2009 June; 17(6):1039-1052.

Bialer G, Horovitz-Fried M, Ya'acobi S, Morgan R A, Cohen C J. Selected murine residues endow human TCR with enhanced tumor recognition. J Immunol. 2010 Jun. 1; 184(11):6232-41.

Bunse M, Bendle G M, Linnemann C, Bies L, Schulz S, Schumacher T N, Uckert W. RNAi-mediated TCR knockdown prevents autoimmunity in mice caused by mixed TCR dimers following TCR gene transfer. Mol Ther. 2014 November; 22(11):1983-91.

Choi et al., Optimization of AAV expression cassettes to improve packaging capacity and transgene expression in neurons. 2014 Mol Brain 7:17-27.

Chung K H, Hart C C, Al-Bassam S, Avery A, Taylor J, Patel P D, Vojtek A B, Turner D L. Polycistronic RNA polymerase II expression vectors for RNA interference based on BIC/miR-155. Nucleic Acids Res. 2006 Apr. 13; 34(7):e53.

Cohen C J, Zhao Y, Zheng Z, Rosenberg S A, Morgan R A. Enhanced antitumor activity of murine-human hybrid T-cell receptor (TCR) in human lymphocytes is associated with improved pairing and TCR/CD3 stability. Cancer Res. 2006 Sep. 1; 66(17):8878-86.

Cohen C J, Li Y F, El-Gamil M, Robbins P F, Rosenberg S A, Morgan R A. Enhanced antitumor activity of T cells engineered to express T-cell receptors with a second disulfide bond. Cancer Res. 2007 Apr. 15; 67(8):3898-903.

Cui, Z., Geurts, A. M., Liu, G., Kaufman, C. D., & Hackett, P. B. (2002). Structure-Function Analysis of the Inverted Terminal Repeats of the Sleeping Beauty Transposon. *Journal of Molecular Biology*, 318(5), 1221-1235.

Data sheet for pCI and pSI mammalian expression vectors, Promega 7/09

Deniger, D. C., Pasetto, A., Tran, E., Parkhurst, M. R., Cohen, C. J., Robbins, P. F., et al. (2016). Stable, non-viral expression of mutated tumor neoantigen-specific T-cell receptors using the Sleeping Beauty transposon/transposase system. Molecular Therapy.

Engels, B., Cam, H., Schüler, T., Indraccolo, S., Gladow, M., Baum, C., et al. (2003). Retroviral vectors for high-level transgene expression in T lymphocytes. *Human Gene Therapy*, 14(12), 1155-1168.

Garrels et al., Cytoplasmic injection of murine zygotes with Sleeping Beauty transposon plasmids and minicircles results in the efficient generation of germline transgenic mice. Biotechnol. J. 2016 (11):178-184.

Ivics Z, Hacket P B, Plasterk R H, Izsvák Z. Molecular reconstruction of Sleeping Beauty, a Tc1-like transposon from fish, and its transposition in human cells. Cell. 1997 Nov. 14; 91(4):501-10.

Kay M A, He C Y, Chen Z Y. A robust system for production of minicircle DNA vectors. Nat Biotechnol. 2010 December; 28(12):1287-9.

Kuball J, Dossett M L, Wolfl M, Ho W Y, Voss R H, Fowler C, Greenberg P D. Facilitating matched pairing and expression of TCR chains introduced into human T cells. Blood. 2007 Mar. 15; 109(6):2331-8.

Leisegang, M., Engels, B., Meyerhuber, P., Kieback, E., Sommermeyer, D., Xue, S.-A., et al. (2008). Enhanced functionality of T cell receptor-redirected T cells is defined by the transgene cassette. *Journal of Molecular Medicine,* 86(5), 573-583.

Liddy N, Bossi G, Adams K J, Lissina A, Mahon T M, Hassan N J, Gavarret J, Bianchi F C, Pumphrey N J, Ladell K, Gostick E, Sewell A K, Lissin N M, Harwood N E, Molloy P E, Li Y, Cameron B J, Sami M, Baston E E, Todorov P T, Paston S J, Dennis R E, Harper J V, Dunn S M, Ashfield R, Johnson A, McGrath Y, Plesa G, June C H, Kalos M, Price D A, Vuidepot A, Williams D D, Sutton D H, Jakobsen B K. Monoclonal TCR-redirected tumor cell killing. Nat Med. 2012 June; 18(6):980-7.

Mátés Ll, Chuah M K, Belay E, Jerchow B, Manoj N, Acosta-Sanchez A, Grzela D P, Schmitt A, Becker K, Matrai J, Ma L, Samara-Kuko E, Gysemans C, Pryputniewicz D, Miskey C, Fletcher B, VandenDriessche T, Ivics Z, Izsvák Z. Molecular evolution of a novel hyperactive Sleeping Beauty transposase enables robust stable gene transfer in vertebrates. Nat Genet. 2009 June; 41(6): 753-61.

Obenaus, M., Leifão C., Leisegang, M., Chen, X., Gavvovidis, I., van der Bruggen, P., et al. (2015). Identification of human T-cell receptors with optimal affinity to cancer antigens using antigen-negative humanized mice, 33(4), Nature biotechnology, 402-407.

Robbins P F, Kassim S H, Tran T L, Crystal J S, Morgan R A, Feldman S A, Yang J C, Dudley M E, Wunderlich J R, Sherry R M, Kammula U S, Hughes M S, Restifo N P, Raffeld M, Lee C C, Li Y F, El-Gamil M, Rosenberg S A. A pilot trial using lymphocytes genetically engineered with an NY-ESO-1-reactive T-cell receptor: long-term follow-up and correlates with response. Clin Cancer Res. 2015 Mar. 1; 21(5):1019-27.

Rosenberg, S. A., Restifo, N. P., Yang, J. C., Morgan, R. A., & Dudley, M. E. (2008). Adoptive cell transfer: a clinical path to effective cancer immunotherapy. *Nature Reviews Cancer,* 8(4), 299-308.

Singh, H., M. J. Figliola, M. J. Dawson, S. Olivares, L. Zhang, G. Yang, S. Maiti, P. Manuri, V. Senyukov, B. Jena, P. Kebriaei, R. E. Champlin, H. Huls, and L. J. N. Cooper. 2013. Manufacture of clinical-grade CD19-specific T cells stably expressing chimeric antigen receptor using Sleeping Beauty system and artificial antigen presenting cells. PLoS ONE. 8:e64138.

Sommermeyer D and Uckert W. Minimal amino acid exchange in human TCR constant regions fosters improved function of TCR gene-modified T cells. J Immunol. 2010 Jun. 1; 184(11):6223-31.

Satrom, P., Ola Snøve, J., Nedland, M., Griinfeld, T. B., Lin, Y., Bass, M. B., & Canon, J. R. (2006). Conserved MicroRNA Characteristics in Mammals. OLIGONUCLEOTIDES, 16(2), 115-144.

Vonderheide R H, June C H. Engineering T cells for cancer: our synthetic future. Immunol Rev. 2014 January 257(1): 7-13.

U.S. Pat. No. 9,181,527; US20070190617; DE 10 2011 118 018 A1.

---

The invention claimed is:

1. A nucleic acid comprising a transposon, wherein the transposon encodes a protein and a miRNA, wherein the nucleic acid encoding the protein comprises an intron comprising sequences encoding the miRNA, wherein expression of the protein and the miRNA is regulated by the same promoter, wherein the nucleic acid is a minicircle DNA.

2. The nucleic acid of claim 1, wherein the nucleic acid is minicircle DNA, comprising less than 5 kb, less than 4 kb, less than 3 kb, or less than 2 kb.

3. The nucleic acid of claim 1, wherein the protein is a TCR construct, wherein, optionally the TCR construct is selected from the group consisting of one TCR alpha chain construct and one TCR beta chain construct; and a single chain TCR construct or a chimeric antigen receptor (CAR), wherein the CAR construct preferably comprises a single chain variable fragment of an antibody (Fv) construct, a spacer region construct and a signaling region construct.

4. The nucleic acid of claim 3, wherein the TCR construct comprises a TCR alpha chain construct and a TCR beta chain construct optimized for pairing with each other, wherein the TCR alpha and beta chains preferably each comprise
   (a) additional Cys residues relative to native human TCRs and/or
   (b) murine amino acid sequences in the constant regions, wherein otherwise, the TCR chains are of human origin.

5. The nucleic acid of claim 1, wherein the transposon encodes at least two miRNAs, optionally, three, four, five, six, seven, eight, nine, ten or more miRNAs.

6. The nucleic acid of claim 1, wherein miRNA encoded by the transposon is capable of silencing expression of a TCR alpha and/or TCR beta chain, wherein the miRNA is not capable of silencing expression of a TCR chain encoded by the transposon, wherein the transposon preferably encodes two miRNAs capable of silencing expression of a TCR alpha and TCR beta chain.

7. The nucleic acid of claim 1, wherein miRNA encoded by the transposon is capable of silencing expression of a protein capable of limiting the therapeutic efficiency of the transferred cells, wherein the protein capable of limiting the therapeutic efficiency of T cells is selected from the group of inhibitory surface receptors comprising CTLA4, PDCD1, LAG3, HAVCR2 and TIGIT, from the group of intracellular proteins that negatively regulate TCR or costimulatory pathways comprising CBLB, CISH, DGK and TNFAIP3, from the group of intracellular proteins that limit cytokine production comprising SPRY2 and CREM or from the group of proteins stabilizing a dysfunctional T cell phenotype comprising MAF, EGR3, NDRG1 and DTX1.

8. The nucleic acid of claim 1, wherein the transposon comprises a cargo nucleic acid flanked by a left and a right inverted repeat/direct repeat (IR/DR), wherein
   (i) the transposon is capable of being mobilized by a Sleeping Beauty transposase protein;
   (ii) the left IR/DR comprises an outer left DR motif and an inner left DR motif, wherein the outer left DR motif comprises the nucleotide sequence of SEQ ID NO:1 and the inner left DR motif comprises the nucleotide sequence of SEQ ID NO: 2; and
   (iii) the right IR/DR comprises an outer right DR motif and an inner right DR motif, wherein the outer right DR motif comprises an inverted sequence of the nucleotide sequence of SEQ ID NO:1 and the inner right DR motif comprises an inverted sequence of the nucleotide sequence of SEQ ID NO: 2.

9. A population of genetically modified cells comprising the nucleic acid of claim 1, wherein the cells are primary T cells.

10. A pharmaceutical composition comprising the population of genetically modified cells of claim 9.

11. The nucleic acid of claim 1, wherein the transposon is capable of being mobilized by a transposase selected from the group of class II transposable elements consisting of piggyBac, Tol2 and Tc1/mariner-type transposons consisting of Frog Prince and Sleeping Beauty transposase.

12. The population of genetically modified cells of claim 9, wherein said population is obtained by electroporating cells with
   a. an mRNA encoding a transposase capable of mobilizing the transposon, and
   b. a nucleic acid comprising a transposon, wherein the transposon encodes a protein and a miRNA, wherein the nucleic acid encoding the protein comprises an intron comprising sequences encoding the miRNA, wherein expression of the protein and the miRNA is regulated by the same promoter, wherein the nucleic acid is a minicircle DNA.

13. The population of genetically modified cells of claim 12, wherein the mRNA encoding the transposase is ivtRNA.

14. A pharmaceutical composition comprising the population of genetically modified cells of claim 12.

15. A method of treating a patient by adoptive T cell therapy, comprising administering the pharmaceutical composition of claim 10 to the patient.

16. A method of treating a patient by adoptive T cell therapy, comprising administering the pharmaceutical composition of claim 14 to the patient.

* * * * *

SEQUENCE LISTING

```
<160> NUMBER OF SEQ ID NOS: 23

<210> SEQ ID NO 1
<211> LENGTH: 32
<212> TYPE: DNA
<213> ORGANISM: Artificial Sequence
<220> FEATURE:
<223> OTHER INFORMATION: pT 4/5 consensus sequence outer DR

<400> SEQUENCE: 1
cagttgaagt cggaagttta catacacytw ag                               32

<210> SEQ ID NO 2
<211> LENGTH: 32
<212> TYPE: DNA
<213> ORGANISM: Artificial Sequence
<220> FEATURE:
<223> OTHER INFORMATION: pT4/5 consensus sequence inner DR

<400> SEQUENCE: 2
yccagtgggt cagaagtgta catacacgvk ct                               32

<210> SEQ ID NO 3
<211> LENGTH: 32
<212> TYPE: DNA
<213> ORGANISM: Artificial Sequence
<220> FEATURE:
<223> OTHER INFORMATION: pT4/5 left outer DR

<400> SEQUENCE: 3
cagttgaagt cggaagttta catacactta ag                               32

<210> SEQ ID NO 4
<211> LENGTH: 32
```

```
<212> TYPE: DNA
<213> ORGANISM: Artificial Sequence
<220> FEATURE:
<223> OTHER INFORMATION: pT4/5 right outer DR

<400> SEQUENCE: 4
cagttgaagt cggaagttta catacacctt ag                                    32

<210> SEQ ID NO 5
<211> LENGTH: 32
<212> TYPE: DNA
<213> ORGANISM: Artificial Sequence
<220> FEATURE:
<223> OTHER INFORMATION: pT4/5 left inner DR

<400> SEQUENCE: 5
tccagtgggt cagaagtgta catacacgvk ct                                    32

<210> SEQ ID NO 6
<211> LENGTH: 32
<212> TYPE: DNA
<213> ORGANISM: Artificial Sequence
<220> FEATURE:
<223> OTHER INFORMATION: pT4/5 right inner DR

<400> SEQUENCE: 6
cccagtgggt cagaagtgta catacacgvk ct                                    32

<210> SEQ ID NO 7
<211> LENGTH: 13
<212> TYPE: DNA
<213> ORGANISM: Artificial Sequence
<220> FEATURE:
<223> OTHER INFORMATION: HDR

<400> SEQUENCE: 7
gtktacakac asd                                                         13

<210> SEQ ID NO 8
<211> LENGTH: 231
<212> TYPE: DNA
<213> ORGANISM: Artificial Sequence
<220> FEATURE:
<223> OTHER INFORMATION: Left IR/DR of pT4 with HDR

<400> SEQUENCE: 8
tacagttgaa gtcggaagtt tacatacacy twagttggag tcattaaaac tcgttttttca     60 actactccac aaatttcttg ttaacaaaca atagttttgg caagtcagtt aggacatcta    120
ctttgtgcat gacacaagtc atttttccaa caattgtkta cakacasdtt atttcactta    180
taattcactg tatcacaaty ccagtgggtc agaagtgtac atacacgvkc t             231

<210> SEQ ID NO 9
<211> LENGTH: 233
<212> TYPE: DNA
<213> ORGANISM: Artificial Sequence
<220> FEATURE:
<223> OTHER INFORMATION: Left IR/DR of pT5 with HDR

<400> SEQUENCE: 9
tatacagttg aagtcggaag tttacataca cytwagttgg agtcattaaa actcgttttt     60
caactactcc acaaatttct tgttaacaaa caatagtttt ggcaagtcag ttaggacatc    120
tactttgtgc atgacacaag tcattttttcc aacaattgtk tacakacasd ttatttcact    180
```

```
tataattcac tgtatcacaa tyccagtggg tcagaagtgt acatacacgv kct            233

<210> SEQ ID NO 10
<211> LENGTH: 232
<212> TYPE: DNA
<213> ORGANISM: Artificial Sequence
<220> FEATURE:
<223> OTHER INFORMATION: Right IR/DR of pT4 without HDR (right IR/DR
      comprises the reverse complement of the given sequences)

<400> SEQUENCE: 10
tacagttgaa gtcggaagtt tacatacacy twagccaaat acatttaaac tcacttttc      60 acaattcctg acatttaatc cgagtaaaga ttccctgtct taaggtcagt taggatcacc    120
actttatttt aagaatgtga aatatcagaa taatagtaga gagaatgatt catttcagct    180
tttatttctt tcatcacatt yccagtgggt cagaagtgta catacacgvk ct            232

<210> SEQ ID NO 11
<211> LENGTH: 233
<212> TYPE: DNA
<213> ORGANISM: Artificial Sequence
<220> FEATURE:
<223> OTHER INFORMATION: Right IR/DR of pT5 without HDR (right IR/DR
      comprises the reverse complement of the given sequences):

<400> SEQUENCE: 11
tatacagttg aagtcggaag tttacataca cytwagccaa atacatttaa actcactttt     60
tcacaattcc tgacatttaa tcctagtaaa aattccctgt cttaggtcag ttaggatcac    120
cactttattt taagaatgtg aaatatcaga ataatagtag agagaatgat tcatttcagc    180
ttttatttct ttcatcacat tyccagtggg tcagaagtgt acatacacgv kct           233

<210> SEQ ID NO 12
<211> LENGTH: 245
<212> TYPE: DNA
<213> ORGANISM: Artificial Sequence
<220> FEATURE:
<223> OTHER INFORMATION: Right IR/DR of pT4 with HDR (right IR/DR
      comprises the reverse complement of the given sequences)

<400> SEQUENCE: 12
tacagttgaa gtcggaagtt tacatacacy twagccaaat acatttaaac tcactttttc     60
acaattcctg acatttaatc cgagtaaaga ttccctgtct taaggtcagt taggatcacc    120
actttatttt aagaatgtga aatatcagaa taatagtaga gagaatgatg tktacakaca    180
sdtcatttca gcttttattt ctttcatcac attyccagtg ggtcagaagt gtacatacac    240 gvkct                                                                245

<210> SEQ ID NO 13
<211> LENGTH: 246
<212> TYPE: DNA
<213> ORGANISM: Artificial Sequence
<220> FEATURE:
<223> OTHER INFORMATION: Right IR/DR of pT5 with HDR (right IR/DR
      comprises the reverse complement of the given sequences)

<400> SEQUENCE: 13
tatacagttg aagtcggaag tttacataca cytwagccaa atacatttaa actcactttt     60
tcacaattcc tgacatttaa tcctagtaaa aattccctgt cttaggtcag ttaggatcac    120
cactttattt taagaatgtg aaatatcaga ataatagtag agagaatgat gtktacakac    180
asdtcatttc agcttttatt ctttcatcac cattyccagt gggtcagaag tgtacataca    240
``` cgvkct        246

<210> SEQ ID NO 14
<211> LENGTH: 6461
<212> TYPE: DNA
<213> ORGANISM: Artificial Sequence
<220> FEATURE:
<223> OTHER INFORMATION: plasmid for minicircle production

<400> SEQUENCE: 14

| | | | | | |
|---|---|---|---|---|---|
| ttgcagaaga | tcctgaacgt | gcagaagaag | ctgcctatca | tccagaagat | catcatcatg | 60 |
| gactctaaga | ccgactacca | gggcttccag | agcatgtaca | cattcgtgac | atctcatctg | 120 |
| cctcctggct | tcaacgagta | cgacttcgtg | ccagagtctt | tcgacaggga | caaaaccatt | 180 |
| gccctgatca | tgaacagctc | tgggtctacc | gagatctgat | atctctagag | tcgagctagc | 240 |
| ttcgaattta | aatcggatcc | ctatacagtt | gaagtcggaa | gtttacatac | accttagcca | 300 |
| aatacattta | aactcacttt | ttcacaattc | ctgacattta | atcctagtaa | aaattccctg | 360 |
| tcttaggtca | gttaggatca | ccactttatt | ttaagaatgt | gaaatatcag | aataatagta | 420 |
| gagagaatga | ttcatttcag | cttttatttc | tttcatcaca | ttcccagtgg | gtcagaagtt | 480 |
| tacatacact | caattagtat | ttggtagcat | tgcctttaaa | ttgtttaact | tgggtcaaac | 540 |
| atttcgagta | gccttccaca | agctagatcc | tgggaataaa | tggcggtaag | atgctcgaat | 600 |
| tacacacaaa | aaaccaacac | acagatgtaa | tgaaaataaa | gatattttat | tgaattctta | 660 |
| cttgtacagc | tcgtccatgc | cgagagtgat | cccggcggcg | gtcacgaact | ccagcaggac | 720 |
| catgtgatcg | cgcttctcgt | tggggtcttt | gctcagggcg | gactgggtgc | tcaggtagtg | 780 |
| gttgtcgggc | agcagcacgg | ggccgtcgcc | gatggggtg | ttctgctggt | agtggtcggc | 840 |
| gagctgcacg | ctgccgtcct | cgatgttgtg | gcggatcttg | aagttcacct | tgatgccgtt | 900 |
| cttctgcttg | tcggccatga | tatagacgtt | gtggctgttg | tagttgtact | ccagcttgtg | 960 |
| ccccaggatg | ttgccgtcct | ccttgaagtc | gatgcccttc | agctcgatgc | ggttcaccag | 1020 |
| ggtgtcgccc | tcgaacttca | cctcggcgcg | ggtcttgtag | ttgccgtcgt | ccttgaagaa | 1080 |
| gatggtgcgc | tcctggacgt | agccttcggg | catggcggac | ttgaagaagt | cgtgctgctt | 1140 |
| catgtggtcg | gggtagcggc | tgaagcactg | cacgccgtag | gtcagggtgg | tcacgagggt | 1200 |
| gggccagggc | acgggcagct | tgccggtggt | gcagatgaac | ttcagggtca | gcttgccgta | 1260 |
| ggtggcatcg | ccctcgccct | cgccggacac | gctgaacttg | tggccgttta | cgtcgccgtc | 1320 |
| cagctcgacc | aggatgggca | ccaccccggt | gaacagctcc | tcgcccttgc | tcaccatgcg | 1380 |
| gccgctggga | gtggacacct | gtggagagaa | aggcaaagtg | gatgtcagta | agaccaatag | 1440 |
| gtgcctatca | gaaacgcaag | agtcttcatg | cattaattac | gcgttctgtc | tcgacaagcc | 1500 |
| cagtttctat | tggtctcctt | aaacctgtct | tgtaaccttg | atacttacct | gcccagtgcc | 1560 |
| tctccggaca | aatgaaagac | ccccgaggtg | ggcagtcaat | cactcagagg | agaccctccc | 1620 |
| aaggaacagc | gagaccacga | gtcggatgca | actgcaagag | ggtttattga | gaacacgggt | 1680 |
| acccgggcga | cgcagtctat | cggaggactg | gcgcgccgag | tgaggggttg | tgggctcttt | 1740 |
| tattgagctc | ggggagcaga | agcgcgcgaa | cagaagcgag | aagcgaactg | attggttagt | 1800 |
| tcaaataagg | cacagggtca | tttcaggtcc | ttggggcacc | ctggaaacat | ctgatggttc | 1860 |
| tctagaaact | gctgagggcg | ggaccgcatc | tgggaccat | ctgttcttgg | ccctgagccg | 1920 |
| gggcaggaac | tgcttaccac | agatatcctg | tttggcccat | attctgctgt | tccaactgtt | 1980 |

```
cttggccctg agccggggca ggaactgctt accacagata tcctgtttgg cccatattct    2040
gctgtctctc tgttcctaac cttgatctga acttctcaag cttctaaagc catgacatca    2100
ttttctggaa ttttccaagc tgtttaaagg cacagtcaac ttagtgtatg taaacttctg    2160
acccactgga attgtgatac agtgaattat aagtgaaata atctgtctgt aaacaattgt    2220
tggaaaaatg acttgtgtca tgcacaaagt agatgtccta actgacttgc caaaactatt    2280
gtttgttaac aagaaatttg tggagtagtt gaaaaacgag ttttaatgac tccaacttaa    2340
gtgtatgtaa acttccgact tcaactgtat agggatccct gcaggagctc gtcgacccat    2400
gggggcccgc cccaactggg gtaacctttg agttctctca gttgggggta atcagcatca    2460
tgatgtggta ccacatcatg atgctgatta taagaatgcg gccgccacac tctagtggat    2520
ctcgagttaa taattcagaa gaactcgtca agaaggcgat agaaggcgat gcgctgcgaa    2580
tcgggagcgg cgataccgta aagcacgagg aagcggtcag cccattcgcc gccaagctct    2640
tcagcaatat cacgggtagc caacgctatg tcctgatagc ggtccgccac acccagccgg    2700
ccacagtcga tgaatccaga aaagcggcca ttttccacca tgatattcgg caagcaggca    2760
tcgccatggg tcacgacgag atcctcgccg tcgggcatgc tcgccttgag cctggcgaac    2820
agttcggctg gcgcgagccc ctgatgctct tcgtccagat catcctgatc gacaagaccg    2880
gcttccatcc gagtacgtgc tcgctcgatg cgatgtttcg cttggtggtc gaatgggcag    2940
gtagccggat caagcgtatg cagccgccgc attgcatcag ccatgatgga tactttctcg    3000
gcaggagcaa ggtgtagatg acatggagat cctgccccgg cacttcgccc aatagcagcc    3060
agtcccttcc cgcttcagtg acaacgtcga gcacagctgc gcaaggaacg cccgtcgtgg    3120
ccagccacga tagccgcgct gcctcgtctt gcagttcatt cagggcaccg gacaggtcgg    3180
tcttgacaaa aagaaccggg cgcccctgcg ctgacagccg aaacacgcg gcatcagagc    3240 agccgattgt ctgttgtgcc cagtcatagc cgaatagcct ctccacccaa gcggccggag    3300
aacctgcgtg caatccatct tgttcaatca tgcgaaacga tcctcatcct gtctcttgat    3360
cagagcttga tccctgcgc catcagatcc ttggcggcga aaagccatc cagtttactt    3420 tgcagggctt cccaacctta ccagagggcg ccccagctgg caattccggt tcgcttgctg    3480
tccataaaac cgcccagtct agctatcgcc atgtaagccc actgcaagct acctgctttc    3540
tctttgcgct tgcgttttcc cttgtccaga tagcccagta gctgacattc atccggggtc    3600
agcaccgttt ctgcggactg ctttctacg tgctcgaggg gggccaaacg gtctccagct    3660
tggctgtttt ggcggatgag agaagatttt cagcctgata cagattaaat cagaacgcag    3720
aagcggtctg ataaaacaga atttgcctgg cggcagtagc gcggtggtcc cacctgaccc    3780
catgccgaac tcagaagtga aacgccgtag cgccgatggt agtgtggggt ctccccatgc    3840
gagagtaggg aactgccagg catcaaataa aacgaaaggc tcagtcgaaa gactgggcct    3900
ttcgttttat ctgttgtttg tcggtgaacg ctctcctgag taggacaaat ccgccgggag    3960
cggatttgaa cgttgcgaag caacggcccg gagggtggcg gcaggacgc ccgccataaa    4020 ctgccaggca tcaaattaag cagaaggcca tcctgacgga tggcctttt gcgtttctac    4080 aaactctttt gtttatttt ctaaatacat tcaaatatgt atccgctcat gaccaaaatc    4140
ccttaacgtg agttttcgtt ccactgagcg tcagaccccg tagaaaagat caaaggatct    4200
tcttgagatc ctttttttct gcgcgtaatc tgctgcttgc aaacaaaaaa accaccgcta    4260
ccagcggtgg tttgtttgcc ggatcaagag ctaccaactc ttttccgaa ggtaactggc    4320 ttcagcagag cgcagatacc aaatactgtc cttctagtgt agccgtagtt aggccaccac    4380
```

```
ttcaagaact ctgtagcacc gcctacatac ctcgctctgc taatcctgtt accagtggct    4440
gctgccagtg gcgataagtc gtgtcttacc gggttggact caagacgata gttaccggat    4500
aaggcgcagc ggtcgggctg aacgggggt tcgtgcacac agcccagctt ggagcgaacg    4560
acctacaccg aactgagata cctacagcgt gagctatgag aaagcgccac gcttcccgaa    4620
gggagaaagg cggacaggta tccggtaagc ggcagggtcg aacaggaga gcgcacgagg    4680 gagcttccag ggggaaacgc ctggtatctt tatagtcctg tcgggtttcg ccacctctga    4740
cttgagcgtc gattttttgtg atgctcgtca ggggggcgga gcctatggaa aaacgccagc    4800
aacgcggcct tttacggtt cctggccttt tgctggcctt ttgctcacat gttctttcct    4860
gcgttatccc ctgattctgt ggataaccgt attaccgcct ttgagtgagc tgataccgct    4920
cgccgcagcc gaacgaccga gcgcagcgag tcagtgagcg aggaagcgga agagcgcctg    4980
atgcggtatt ttctccttac gcatctgtgc ggtatttcac accgcatatg gtgcactctc    5040
agtacaatct gctctgatgc cgcatagtta agccagtata cactccgcta tcgctacgtg    5100
actgggtcat ggctgcgccc cgacacccgc caacacccgc tgacgcgccc tgacgggctt    5160
gtctgctccc ggcatccgct tacagacaag ctgtgaccgt ctccgggagc tgcatgtgtc    5220
agaggttttc accgtcatca ccgaaacgcg cgaggcagca gatcaattcg cgcgcgaagg    5280
cgaagcggca tgcataatgt gcctgtcaaa tggacgaagc agggattctg caaacccctat    5340 gctactccgt caagccgtca attgtctgat tcgttaccaa ttatgacaac ttgacggcta    5400
catcattcac ttttttcttca aaccggcac ggaactcgct cgggctggcc ccggtgcatt    5460
ttttaaatac ccgcgagaaa tagagttgat cgtcaaaacc aacattgcga ccgacggtgg    5520
cgataggcat ccgggtggtg ctcaaaagca gcttcgcctg gctgatacgt tggtcctcgc    5580
gccagcttaa gacgctaatc cctaactgct ggcggaaaag atgtgacaga cgcgacggcg    5640
acaagcaaac atgctgtgcg acgctggcga tacattaccc tgttatccct agatgacatt    5700
accctgttat cccagatgac attaccctgt tatccctaga tgacattacc ctgttatccc    5760
tagatgacat ttaccctgtt atccctagat gacattaccc tgttatccca gatgacatta    5820
ccctgttatc cctagataca ttaccctgtt atcccagatg acatacccctg ttatccctag    5880 atgacattac cctgttatcc cagatgacat taccctgtta tccctagata cattaccctg    5940
ttatcccaga tgacataccc tgttatccct agatgacatt accctgttat cccagatgac    6000
attaccctgt tatccctaga tacattaccc tgttatccca gatgacatac cctgttatcc    6060
ctagatgaca ttaccctgtt atcccagatg acattaccct gttatcccta gatacattac    6120
cctgttatcc cagatgacat accctgttat ccctagatga cattaccctg ttatcccaga    6180
tgacattacc ctgttatccc tagatacatt accctgttat cccagatgac ataccctgtt    6240
atccctagat gacattaccc tgttatccca gatgacatta ccctgttatc cctagataca    6300
ttaccctgtt atcccagatg acataccctg ttatccctag atgacattac cctgttatcc    6360
cagataaact caatgatgat gatgatgatg gtcgagactc agcggccgcg gtgccagggc    6420
gtgcccttgg gctccccggg cgcgactagt gaattcagat c                        6461
```

<210> SEQ ID NO 15
<211> LENGTH: 22
<212> TYPE: DNA
<213> ORGANISM: Artificial Sequence
<220> FEATURE:
<223> OTHER INFORMATION: TCRα-specific antisense sequence

<400> SEQUENCE: 15
tgaaagttta ggttcgtatc tg                                              22

<210> SEQ ID NO 16
<211> LENGTH: 22
<212> TYPE: DNA
<213> ORGANISM: Artificial Sequence
<220> FEATURE:
<223> OTHER INFORMATION: TCRβ-specific antisense sequence

<400> SEQUENCE: 16
tctgatggct caaacacagc ga                                              22

<210> SEQ ID NO 17
<211> LENGTH: 149
<212> TYPE: DNA
<213> ORGANISM: Artificial Sequence
<220> FEATURE:
<223> OTHER INFORMATION: miR-155

<400> SEQUENCE: 17
cttatcctct ggctgctgga ggcttgctga aggctgtatg ctgtgaaagt ttaggttcgt     60
atctgttttg gcctctgact gacagatacg aataaacttt cacaggacac aaggcctgtt    120
actagcactc acatggaaca aatggccac                                      149

<210> SEQ ID NO 18
<211> LENGTH: 157
<212> TYPE: DNA
<213> ORGANISM: Artificial Sequence
<220> FEATURE:
<223> OTHER INFORMATION: artificial miRNA

<400> SEQUENCE: 18
caagagaaca aagtggagtc tttgttgccc acacccagct tccctggctc tctgatggct     60
caaacacagc gagtacatga gacacgctgt gtttcagcca tcggtgagct gggaagcat    120 ctgcagcaga gcctgcctgg tggcccctga gagattt                             157

<210> SEQ ID NO 19
<211> LENGTH: 312
<212> TYPE: DNA
<213> ORGANISM: Artificial Sequence
<220> FEATURE:
<223> OTHER INFORMATION: miRNA construct for silencing expression of
      human TCR a and b chains

<400> SEQUENCE: 19
cttatcctct ggctgctgga ggcttgctga aggctgtatg ctgtgaaagt ttaggttcgt     60
atctgttttg gcctctgact gacagatacg aataaacttt cacaggacac aaggcctgtt    120
actagcactc acatggaaca aatggccaca cgcgccaaga gaacaaagtg gagtctttgt    180
tgcccacacc cagcttccct ggctctctga tggctcaaac acagcgagta catgagacac    240
gctgtgtttc agccatcggt gagcttggga agcatctgca gcagagcctg cctggtggcc    300
cctgagagat tt                                                        312

<210> SEQ ID NO 20
<211> LENGTH: 9
<212> TYPE: PRT
<213> ORGANISM: Artificial Sequence
<220> FEATURE:
<223> OTHER INFORMATION: MAGE-A1278 -specific peptide -continued

<400> SEQUENCE: 20

Lys Val Leu Glu Tyr Val Ile Lys Val
1               5

<210> SEQ ID NO 21
<211> LENGTH: 9
<212> TYPE: PRT
<213> ORGANISM: Artificial Sequence
<220> FEATURE:
<223> OTHER INFORMATION: tyrosinase-specific control peptide Tyr369

<400> SEQUENCE: 21

Tyr Met Asp Gly Thr Met Ser Gln Val
1               5

<210> SEQ ID NO 22
<211> LENGTH: 6417
<212> TYPE: DNA
<213> ORGANISM: Artificial Sequence
<220> FEATURE:
<223> OTHER INFORMATION: pSB-miR-TCR1367co

<400> SEQUENCE: 22

```
caaggcgatt aagttgggta acgccagggt tttcccagtc acgacgttgt aaaacgacgg     60
ccagtgagcg cgcgtaatac gactcactat agggcgaatt ggagctcgga tccctataca    120
gttgaagtcg gaagtttaca tacacttaag ttggagtcat aaaactcgt ttttcaacta     180
ctccacaaat ttcttgttaa caaacaatag ttttggcaag tcagttagga catctacttt    240
gtgcatgaca caagtcattt ttccaacaat tgtttacaga cagattattt cacttataat    300
tcactgtatc acaattccag tgggtcagaa gtttacatac actaagttga ctgtgccttt    360
aaacagcttg gaaaattcca gaaaatgatg tcatggcttt agaagcttga gaagttcaga    420
tcaaggttag gaacagagag acagcagaat atgggccaaa caggatatct gtggtaagca    480
gttcctgccc cggctcaggg ccaagaacag ttggaacagc agaatatggg ccaaacagga    540
tatctgtggt aagcagttcc tgccccggct cagggccaag aacagatggt ccccagatgc    600
ggtcccgccc tcagcagttt ctagagaacc atcagatgtt tccagggtgc cccaaggacc    660
tgaaatgacc ctgtgcctta tttgaactaa ccaatcagtt cgcttctcgc ttctgttcgc    720
gcgcttctgc tccccgagct caataaaaga gcccacaacc cctcactcgg cgcgccagtc    780
ctccgataga ctgcgtcgcc cgggtacccg tgttctcaat aaaccctctt gcagttgcat    840
ccgactcgtg gtctcgctgt tccttgggag ggtctcctct gagtgattga ctgcccacct    900
cgggggtctt tcatttgtcc ggagaggcac tgggcaggta agtatcaagg ttacaagaca    960
ggtttaagga gaccaataga aactgggctt gtcgagacag aacgcgcctt atcctctggc   1020
tgctggaggc ttgctgaagg ctgtatgctg tgaaagttta ggttcgtatc tgttttggcc   1080
tctgactgac agatacgaat aaactttcac aggacacaag gcctgttact agcactcaca   1140
tggaacaaat ggccacacgc gccaagagaa caaagtggag tctttgttgc ccacacccag   1200
cttccctggc tctctgatgg ctcaaacaca gcgagtacat gagacacgct gtgtttcagc   1260
catcggtgag cttgggaagc atctgcagca gagcctgcct ggtggcccct gagagattta   1320
cgcgtaatta atgcatgaag actcttgcgt ttctgatagg cacctattgg tcttactgac   1380
atccactttg cctttctctc cacaggtgtc cactcccagc ggccgccacc atgggaatca   1440
gactgctgtg cagagtggcc ttctgcttcc tggccgtggg cctggtggac gtgaaagtga   1500
cccagagcag cagataccte gtgaagcgga ccggcgagaa ggtgttcctg gaatgcgtgc   1560
```

```
aggacatgga ccacgagaat atgttctggt acagacagga ccccggcctg ggcctgcggc    1620
tgatctactt cagctacgac gtgaagatga aggaaaaggg cgacatcccc gagggctaca    1680
gcgtgtccag agagaagaaa gagcggttca gcctgatcct ggaaagcgcc agcaccaacc    1740
agaccagcat gtacctgtgc gccagcagag gcctggccgg ctacgagcag tattttggcc    1800
ctggcacccg gctgaccgtg accgaggatc tgaagaacgt gttccccca gaggtggccg    1860 tgttcgagcc ttctgaggcc gagatcagcc acacccagaa agccaccctc gtgtgtctgg    1920
ccaccggctt ctaccccgac cacgtggaac tgtcttggtg ggtcaacggc aaagaggtgc    1980
acagcggcgt gtccaccgat ccccagcctc tgaaagaaca gcccgccctg aacgacagcc    2040
ggtactgcct gtccagcaga ctgagagtgt ccgccacctt ctggcagaac ccccggaacc    2100
acttcagatg ccaggtgcag ttctacggcc tgagcgagaa cgacgagtgg acccaggaca    2160
gagccaagcc cgtgacacag atcgtgtctg ccgaagcctg ggcagagcc gattgcggct    2220 ttaccagcga gagctaccag cagggcgtgc tgagcgccac catcctgtac gagatcctgc    2280
tgggcaaggc caccctgtac gccgtgctgg tgtctgccct ggtgctgatg gccatggtca    2340 gcgaagga ctccagaggc ggaagcggcg ccaccaactt cagcctgctg aaacaggccg    2400
gcgacgtgga agagaaccct ggccccatga agacttcgcc ggcttcagct tcctgttcct    2460
gtggctgcag ctggactgca tgagcagagg cgaggacgtg aacagagcc tgttctgag    2520 cgtgcgcgag ggcgacagca gcgtgatcaa ttgcacctac accgacagct ccagcaccta    2580
cctgtactgg tacaagcagg aacctggcgc cggactgcag ctgctgacct acatcttcag    2640
caacatggac atgaagcagg accagagact gaccgtgctg ctgaacaaga aggacaagca    2700
cctgagcctg cggatcgccg atacccagac aggcgacagc gccatctact tttgcgccga    2760
gagcatcggc agcaacagcg gctacgccct gaatttcggc aagggcacaa gcctgctcgt    2820 gacccccac atccagaacc ctgaccctgc cgtgtaccag ctgcgggaca gcaagagcag    2880
cgacaagagc gtgtgcctgt tcaccgactt cgacagccag accaacgtgt cccagagcaa    2940
ggacagcgac gtgtacatca ccgacaagac agtgctggac atgcggagca tggacttcaa    3000
gagcaactcc gccgtggctt ggagcaacaa gagcgacttc gcctgcgcca acgccttcaa    3060
caacagcatt atccctgagg acacattctt cccaagcccc gagagcagct gtgacgtgaa    3120
gctggtggaa aagagcttcg agacagacac caacctgaac ttccagaacc tgagcgtgat    3180
cggcttcaga atcctgctgc tgaaggtggc cggcttcaac ctgctgatga ccctgagact    3240
gtggtccagc tgaattcaat aaaatatctt tattttcatt acatctgtgt gttggttttt    3300
tgtgtgtaat tcggatctag cttgtggaag gctactcgaa atgtttgacc caagttaaac    3360
aatttaaagg caatgctacc aaatactaat gagtgtatg taaacttctg acccactggg    3420
aatgtgatga agaaataaa agctgaaatg aatcattctc tctactatta ttctgatatt    3480
tcacattctt aaaataaagt ggtgatccta actgacctaa acagggaat ttttactagg    3540 attaaatgtc aggaattgtg aaaaagtgag tttaaatgta tttggctaag gtgtatgtaa    3600
acttccgact tcaactgtat agggatcctc tagctagagt cgacctcgag gggggcccg    3660 gtacccagct tttgttccct ttagtgaggg ttaatttcga gcttggcgta atcatggtca    3720
tagctgtttc ctgtgtgaaa ttgttatccg ctcacaattc cacacaacat acgagccgga    3780
agcataaagt gtaaagcctg gggtgcctaa tgagtgagct aactcacatt aattgcgttg    3840
cgctcactgc ccgctttcca gtcgggaaac ctgtcgtgcc agctgcatta atgaatcggc    3900
```

```
caacgcgcgg ggagaggcgg tttgcgtatt gggcgctctt ccgcttcctc gctcactgac    3960
tcgctgcgct cggtcgttcg gctgcggcga gcggtatcag ctcactcaaa ggcggtaata    4020
cggttatcca cagaatcagg ggataacgca ggaaagaaca tgtgagcaaa aggccagcaa    4080
aaggccagga accgtaaaaa ggccgcgttg ctggcgtttt tccataggct ccgcccccct    4140
gacgagcatc acaaaaatcg acgctcaagt cagaggtggc gaaacccgac aggactataa    4200
agataccagg cgtttccccc tggaagctcc ctcgtgcgct ctcctgttcc gaccctgccg    4260
cttaccggat acctgtccgc ctttctccct tcgggaagcg tggcgctttc tcatagctca    4320
cgctgtaggt atctcagttc ggtgtaggtc gttcgctcca agctgggctg tgtgcacgaa    4380
ccccccgttc agcccgaccg ctgcgcctta tccggtaact atcgtcttga gtccaacccg    4440
gtaagacacg acttatcgcc actggcagca gccactggta acaggattag cagagcgagg    4500
tatgtaggcg gtgctacaga gttcttgaag tggtggccta actacggcta cactagaagg    4560
acagtatttg gtatctgcgc tctgctgaag ccagttacct tcggaaaaag agttggtagc    4620
tcttgatccg gcaaacaaac caccgctggt agcggtggtt tttttgtttg caagcagcag    4680
attacgcgca gaaaaaaagg atctcaagaa gatcctttga tcttttctac ggggtctgac    4740
gctcagtgga acgaaaactc acgttaaggg attttggtca tgagattatc aaaaaggatc    4800
ttcacctaga tccttttaaa ttaaaaatga agttttaaat caatctaaag tatatatgag    4860
taaacttggt ctgacagtta ccaatgctta atcagtgagg cacctatctc agcgatctgt    4920
ctatttcgtt catccatagt tgcctgactc cccgtcgtgt agataactac gatacgggag    4980
ggcttaccat ctggccccag tgctgcaatg ataccgcgag acccacgctc accggctcca    5040
gatttatcag caataaacca gccagccgga agggccgagc gcagaagtgg tcctgcaact    5100
ttatccgcct ccatccagtc tattaattgt tgccgggaag ctagagtaag tagttcgcca    5160
gttaatagtt tgcgcaacgt tgttgccatt gctacaggca tcgtggtgtc acgctcgtcg    5220
tttggtatgg cttcattcag ctccggttcc caacgatcaa ggcgagttac atgatccccc    5280
atgttgtgca aaaaagcggt tagctccttc ggtcctccga tcgttgtcag aagtaagttg    5340
gccgcagtgt tatcactcat ggttatggca gcactgcata attctcttac tgtcatgcca    5400
tccgtaagat gcttttctgt gactggtgag tactcaacca agtcattctg agaatagtgt    5460
atgcggcgac cgagttgctc ttgcccggcg tcaatacggg ataataccgc gccacatagc    5520
agaactttaa aagtgctcat cattggaaaa cgttcttcgg ggcgaaaact ctcaaggatc    5580
ttaccgctgt tgagatccag ttcgatgtaa cccactcgtg cacccaactg atcttcagca    5640
tcttttactt tcaccagcgt ttctgggtga gcaaaaacag gaaggcaaaa tgccgcaaaa    5700
aagggaataa gggcgacacg gaaatgttga atactcatac tcttcctttt tcaatattat    5760
tgaagcattt atcagggtta ttgtctcatg agcggataca tatttgaatg tatttagaaa    5820
aataaacaaa taggggttcc gcgcacattt ccccgaaaag tgccacctga cgcgccctgt    5880
agcggcgcat taagcgcggc gggtgtggtg gttacgcgca gcgtgaccgc tacacttgcc    5940
agcgccctag cgcccgctcc tttcgctttc ttcccttcct ttctcgccac gttcgccggc    6000
tttccccgtc aagctctaaa tcgggggctc cctttagggt tccgatttag tgctttacgg    6060
cacctcgacc ccaaaaaact tgattagggt gatggttcac gtagtgggcc atcgccctga    6120
tagacggttt ttcgcccttt gacgttggag tccacgttct ttaatagtgg actcttgttc    6180
caaactggaa caacactcaa ccctatctcg gtctattctt ttgatttata agggattttg    6240
ccgatttcgg cctattggtt aaaaaatgag ctgatttaac aaaaatttaa cgcgaatttt    6300
```

```
aacaaaatat taacgcttac aatttccatt cgccattcag gctgcgcaac tgttgggaag    6360
ggcgatcggt gcgggcctct tcgctattac gccagctggc gaaaggggga tgtgctg      6417

<210> SEQ ID NO 23
<211> LENGTH: 1824
<212> TYPE: DNA
<213> ORGANISM: Artificial Sequence
<220> FEATURE:
<223> OTHER INFORMATION: TCR1367, codon-optized, minimally murinized,
      additional cysteine bridge

<400> SEQUENCE: 23
atgggaatca gactgctgtg cagagtggcc ttctgcttcc tggccgtggg cctggtggac      60
gtgaaagtga cccagagcag cagataccte gtgaagcgga ccggcgagaa ggtgttcctg     120
gaatgcgtgc aggacatgga ccacgagaat atgttctggt acagacagga ccccggcctg     180
ggcctgcggc tgatctactt cagctacgac gtgaagatga aggaaaaggg cgacatcccc     240
gagggctaca gcgtgtccag agagaagaaa gagcggttca gcctgatcct ggaaagcgcc     300
agcaccaacc agaccagcat gtacctgtgc gccagcagag gcctggccgg ctacgagcag     360
tattttggcc ctggcacccg gctgaccgtg accgaggacc tgaagaacgt gttccccccc     420
gaggtggccg tgttcgagcc cagcaaggcc gagatcgccc acacccagaa agccaccctg     480
gtgtgcctgg ccaccggctt ctaccccgac cacgtgaacc tgtcttggtg ggtgaacggc     540
aaagaggtgc acagcggcgt gtgtaccgac ccccagcccc tgaaagagca gcctgccctg     600
aacgactccc ggtactgcct gagcagccgg ctgagagtgt ccgccacctt ctggcagaac     660 cccccggaacc acttcagatg ccaggtgcag ttctacggcc tgagcgagaa cgacgagtgg     720
acccaggacc gggccaagcc cgtgacccag attgtgtctg ccgaggcctg ggcagagct     780 gattgtggca tcaccagcgc cagctaccac cagggcgtgc tgagcgccac catcctgtac     840
gagatcctgc tggcaaggc caccctgtac gccgtgctgg tgtccgccct ggtgctgatg     900
gccatggtga acggaagga cagcagaggc ggcagcggcg ccaccaactt tagcctgctg     960
aaacaggccg cgacgtggga agagaaccct ggccccatga agaccttcgc cggcttcagc    1020
ttcctgttcc tgtggctgca gctggactgc atgagcaggg gcgaggacgt ggaacagagc    1080
ctgtttctga gcgtgcgcga gggcgacagc gcgtgatca attgcaccta caccgacagc    1140
tccagcacct acctgtactg gtacaagcag gaacctggcg ccggactgca gctgctgacc    1200
tacatcttca gcaacatgga catgaagcag gaccagagac tgaccgtgct gctgaacaag    1260
aaggacaagc acctgagcct gcggatcgcc gatacccaga caggcgacag cgccatctac    1320
ttttgcgccg agagcatcgg cagcaacagc ggctacgccc tgaacttcgg caagggcaca    1380
agcctgctcg tgacccctca catccagaac cccgaccccg ccgtgtacca gctgcgggac    1440
agcaagagca gcgacaagag cgtgtgcctg ttcaccgact cgacagcca gaccaacgtg    1500 tcccagagca aggacagcga cgtgtacatc accgacaagt gcgtgctgga catgcggagc    1560
atggacttca agagcaactc cgccgtggcc tggtccaaca gagcgactt cgcctgcgcc    1620 aacgccttca caacagcat catccccgag gacacattct cccccagctc cgacgtgccc    1680
tgcgacgtga gctggtggga aaagagcttc gagacagaca ccaacctgaa cttccagaac    1740
ctgagcgtga tcggcttcag aatcctgctg ctgaaggtgg ctggcttcaa cctgctgatg    1800
accctgcggc tgtggagcag ctga                                          1824
```